United States Patent [19]
Popovich et al.

[11] Patent Number: 5,261,876
[45] Date of Patent: Nov. 16, 1993

[54] ENHANCED PERITONEAL MEMBRANE PLASMAPHERESIS

[75] Inventors: Robert P. Popovich, Austin; Jack W. Moncrief, South Austin; Zhengzhi He, Austin, all of Tex.

[73] Assignee: Moncrief-Popovich Research Institute, Inc., Austin, Tex.

[21] Appl. No.: 899,676

[22] Filed: Jun. 12, 1992

[51] Int. Cl.$^5$ .............................................. A61M 1/00
[52] U.S. Cl. .................................... 604/28; 604/29
[58] Field of Search ............................... 604/4–6, 604/28, 29, 48, 49

[56] References Cited

U.S. PATENT DOCUMENTS

| | | | |
|---|---|---|---|
| 4,133,891 | 1/1979 | Nolph | 604/28 |
| 4,673,385 | 6/1987 | Popovich et al. | 604/28 |
| 4,832,684 | 5/1989 | Popovich et al. | 604/28 |
| 5,057,075 | 10/1991 | Moncrief et al. | 604/49 |

OTHER PUBLICATIONS

Agnew, A. et al., Dorland's Illustrated Medical Dictionary, Saunders, Philadelphia, 412 (1965).
Allen, I. and Weatherford, T., "Role of fenestrated basement membrane in lymphatic absorption from peritoneal cavity," *Am. J. of Physiol.* 197:551–554, 1959.
Aune, S., "Transperitoneal Exchange, III. The Influence of Transperitoneal Fluid Flux on the Peritoneal Plasma Clearance of Serum Albrumin in Rabbits," *Scand. J. Gastroent*, 5:105–113, 1970.
Babb, A. L., et al., "Bidirectional Permeability of the Human Peritoneum to Middle Molecules," *Proc. Eur. Dial. and Transpl. Assoc.* 247–262, 1973.
Bambauer, R. et al., "Indications of Plasmapheresis and Selection of Different Substitution Solutions," *Biomat. Art. Cells and Art. Org.*, 17(1) 9–27, 1989.
Bird, R. B., et al., "Interphase Transport in Multicomponent Systems," *Transport Phenomena*, John Wiley and Sons, New York, Chapter 21, 626–676, 1960.
Breborowicz, A. et al., "Augmentation of Peritoneal Dialysis Clearance with Procaine," *Kid. Int.* 26:392–396, 1984.
Breborowicz, A. et al., "Functional Differentiation of Rabbit Peritoneum Investigations in vitro.," *Acta Med. Pol.* 25:11–15, 1984.
Breborowicz, A. et al., "Intracellular calcium ions modulate permeability of the peritoneal mesothelium in vitro," *Perit. Dial. Bull.* 5(2):105–108, 1985.
Breborowicz, A. et al., "Permeability of Different Parts of the Peritoneal Mesothelium to Solutes," An in vitro study. *Per. Dia. Int.*, vol. 9:135–141, 1989.
Brown, E. A. et al., "Effects of hypertonic dialysate and vasodilators on Peritoneal Dialysis Clearances in Rate," *Kid. Int.* 13:271–277, 1978.
Chen, L. T., et al., "Chronic End–Stage Renal Failure," Heilongjiang People's Press. 1–5, 1981. (written in Chinese).
Chou, C. C. et al., "Physiological and Pharmacological Alternations in Gastrointestinal Blood Flow," *Measurement of Blood Flow: Applications to The Splanchnic Circulation*, Williams & Wilkins Pub., Chapter 27:477–509, 1981.

(List continued on next page.)

Primary Examiner—C. Fred Rosenbaum
Assistant Examiner—Michael Rafa
Attorney, Agent, or Firm—Arnold, White & Durkee

[57] ABSTRACT

The method of treatment called peritoneal membrane plasmapheresis for removal of plasma proteins is enhanced by specification of a sequence of two or three solutions for instilling into and draining from the peritoneal cavity. Solution 1 contains a vosodilator, solution 3 contains no vasoactive drug, and solution 2 contains a vasoconstrictor. Choice of the sequence of solutions to be instilled and drained according to the claimed methods results in sustained opening of peritoneal membrane pores and substantially elevated rates of plasma protein removal, avoiding the problem of declining rates due to local tissue compensatory mechanisms which are observed when only solution 1 is used. Resulting protein removal rates in an anticoagulated patient compare favorably with those attainable with extracorporeal phasmapheresis. An analogous process may be carried out to increase the pore size of any biological membrane accessible to the solutions.

43 Claims, 20 Drawing Sheets

Protein Removal on a Daily Basis

OTHER PUBLICATIONS

Clark, A. J., "Absorption From the Peritoneal Cavity," *J. Pharm. Exp. Ther.* 16:415–433, 1921.

Courtice, F. C. and Steinbeck, A. W., "The Lymphatic Drainage of Plasma From the Peritoneal Cavity of the Cat," *Austral. J. Exp. Biol. Med. Sci.* 28:161–169, 1950.

Diaz-Buxo, J. A. et al., "Home Dialysis-The Best Alternative?," *Dialysis & Transplantation* 9(9):812, 814 (1980).

Diaz-Buxo, J. A., "Continuous cyclic peritoneal dialysis," *Peritoneal Dialysis* 2nd Rev. Edition, Martinus Nijhoff Publ., 247–266 (9185).

Drukker, W., "Haemodialysis: A Historical Review," *Replacement of Renal Functions by Dialysis 2nd Rev. Edition*, Martinus Nijhoff Pub., 3–52, 1978.

Flessner, M. F. et al., "Peritoneal lymphatic uptake of fibrinogen and erythrocytes in the rat," *Am. J. Physiol.* 244:H89–H96, 1983.

Flessner, M. F. et al., "Exchange of micromolecules between peritoneal cavity and plasma," *Am. J. Physiol.* 248:H15–H25, 1985.

Ganter, G., "Ueber die Beseitigung giftiger Stoffe aus dem Blut durch Dialyse," *Munch Med Wochschr*, 70:1478–1480, 1923. (written in German).

Goldberg, L. I., "Cardiovascular and Renal Actions of Dopamine: Potential Clinical Implications," *Pharmacol. Rev.* 24(1):1–30, 1972.

Goldschmidt, Z. H. et al., "Effect of Dialysate Volume on Peritoneal Dialysis Kinetics," *Kid. Int.* 5:240–245, 1974.

Gosselin, R. E. et al., "Diffusional Transport of Solutes Through Mesentery and Periotoneum," *J. Theoret. Biol.* 3:487–495, 1962.

Granger, D. N. et al., "Peritoneal Dialysis Solutions and Feline Splanchnic Blood flow," *Clin. Exp. Pharmacol. & Phys.* 11:473–481, 1984.

Gray, H., "The Abdomen," *Anatomy of the Human Body*, 27th Ed., Lea & Febiger Pub., Philadelphia, 1253–1272, 1959.

Gross, M. and McDonald, H. P., "Effect of Dialysate Temperature and Flow Rate on Peritoneal Clearance," *JAMA*, 202(4):363–365, 1967.

Hart, W. et al., "Estimating the cost of expanding an apheresis program," *Transfusions* 31(6):538–541, 1991.

He, Z., "Pharmacological Enhancement of Peritoneal Mass Transfer," Austin, Texas, University of Texas, Ph.D. dissertation, 1991.

Huang, Di, et al., "Classic of Internal Medicine," *Press of People's Health*, Chapter 74:503–547, 1963. (written in Chinese).

Henderson, L. W. and Nolph, K. D., "Altered Permeability of Peritoneal Membrane after using Hypertonic Peritoneal Dialysis Fluid," *J. Clin. Invest.* 48:992–1001, 1976.

Kallen, R. J., "A Method for Approximating the Efficacy of Peritoneal Dialysis for Uremia," *Am. J. Dis. Child* III:156–160, 1966.

Karnovsky, M. J., "The Ultrastructural Basis of Capillary Permeability Studied with Peroxides as a Tracer," *J. Cell. Biol.* 35(1):213–236, 1967.

Korthuis, R. J. and Granger, D. N., "Role of the Peritoneal Microcirculation in Peritoneal Dialysis," *Peritoneal Dialysis*, Kluwer Acad. Pub., 28–47, 1989.

Leak, L. V. and Rahil, K., "Permeability of the Diaphragmatic Mesothelium," The Ultrastructural Basia for Stomata. *Am. J. Anat.*, 151:557–592, 1978.

Legrain, J. and Jacobs, C., "Place of chronic ambulatory peritoneal dialysis in the treatment of end stage renal failure," *Continuous Ambulatory Peritoneal Dialysis, Proceedings of an International Symposium*, Paris, Nov. 2–3, 1979, 347–353, 1979.

Lieb, W. R. and Stein, W. D., "Biological Membranes Behave as Nonporous Polymeric Sheets with Respect to the Diffusion of Nonelectrolyte," *Nature* 224:240–243, 1969.

Mactier, R., et al., "Role of Peritoneal Cavity Lymphatic Absorption in Peritoneal Dialysis," *Kid. Int.* 32:165–172, 1987.

Maher, J. F. et al., "Isoproterenol Enhancement of Peritoneal Permeability," *J. of Dial.* 1(4):319–331, 1977.

Maher, J. F. and Hirszel, P., "Augmentation of peritoneal clearances by drugs," *Continuous Ambulatory Peritoneal Dialysis, Proceedings of an International Symposium*, Paris, Nov. 2–3, 1979, 42–46, 1979.

Maher, J. F., "Peritoneal Transport Rates: Mechanisms, Limitation and Methods for Augmentation," *Kid. Int.* 18(10):S–117–S–121, 1980.

Maher, J. F. and Hirszel, P., "Pharmacologic manipulation of peritoneal transport," Peritoneal Dialysis, 2nd Rev. Ed., Martinus Nijhoff Pub., 267–296, 1985.

(List continued on next page.)

OTHER PUBLICATIONS

Malchesky, P. S. and Nose, Y., "Biomodulation Effects of Extracorporeal Circulation in Apheresis," *Seminars in Hematology*, 26(2) Sup. 1 (Apr.): 42–51, 1989.

Miller, F. N. et al., "Effects of Peritoneal Dialysis Solutions on Human Clearances and Rat Arterioles," Trans. Am. Soc. Artif. Intern. Organs XXVI:131–132, 1978.

Miller, F. N. et al., "Microvascular and clinical effects of altered peritoneal dialysis solution," *Kid. Int.* 15:630–639, 1979.

Miller, F. N. et al., "Hyperosmolality, acetate and lactate: Dilatory factors during peritoneal dialysis," *Kid. Int.* 20:397–402, 1981.

Miller, F. N., "The peritoneal microcirculation," *Peritoneal Dialysis* 2nd Rev. Ed., Martinus Nijhoff Pub., 51–93, 1985.

Moncrief, J. W. and Popovich, R. P., "Continuous Ambulatory and Peritoneal Dialysis (CAPD)", *Peritoneal Dialysis*, Third Ed., Kluwer Acad. Pub., 152–168, 1989.

Moncrief, et al., "The History and Current Status of Continuous Ambulatory Peritoneal Dialysis," *Am. J. of Kid. Dis.*, vol. XVI, No. 6 (Dec.):579–584, 1990.

Morgenstern, B. Z. et al., "Convective Characteristics of Pediatric Peritoneal Dialysis," *Perit. Dial. Bull.-Supp.*, 4:S155–S158, 1984.

Nagel, W. and Kuschinsky, W., "Study of the Permeability of Isolated Dog Mesentery," *Eur. J. Clin. Invest.*, 1:149–154, 1970.

Nakamura, Y. and Wayland, H., "Macromolecular Transport in the Cat Mesentery," *Microvasc. Res.* 9:1–21, 1975.

Nolph, K. D., "Effects of Intraperitoneal Vasodilators on Peritoneal Clearances," *Dial. & Transpl.* 7(8):812–817, 1978.

Nolph, K. D. et al., "Determinants of low clearances of small solutes during peritoneal dialysis," *Kid. Int.* 13:117–123, 1978.

Nolph, K. D. et al., "Effects of Intraperitoneal Nitroprusside on Peritoneal Clearances in Man with Variations in Dose, Frequency of Administration, and Dwell Times," *Nephron* 24:114–200, 1979.

Nolph, K. D. et al., "Equilibration of peritoneal dialysis solutions during long dwell exchange," *J. Lab. Clin. Med.* 93:246–256, 1979.

Nolph, K. D. and Sorkin, M. I., "Continuous ambulatory peritoneal dialysis," *Chronic Renal Failure*, Churchill Livingstone Pub., Chapter 7:193–217, 1981.

Nolph K. D. et al., "The kinetics of ultrafiltration during peritoneal dialysis: The role of lymphatics," *Kid. Int.* 32:219–226, 1987.

Nolph, K. D. and Twardowski, Z. J., "The Peritoneal Dialysis System," *Peritoneal Dialysis*, Third Ed., Kluwer Academic Pub., 13–27, 1989.

Olin, T. and Saldeen, T., "The Lymphatic Pathways from the Peritoneal Cavity: A Lymphangiographic Study in the Rat," *Cancer Res.* 24:1700–1711, 1964.

Popovich, R. P. et al., "The Genesis of the Square Meter-Hour Hypothesis," Trans. Amer. Soc. Aritf. Int. Organs, vol. XVII:81–91, 1971.

Popovich, R. P. et al., "A Model of the Peritoneal Dialysis System," Proc. 25th *Ann. Conf. on Engr. in Med. and Biol.*, 14:172, 1972.

Popovich, R. P. et al., "Physiological Transport Parameters in Peritoneal and Hemodialysis," The University of Texas, College of Engineering, 2nd Ann. Rep. No. NO1-AM-3-2205, 1977.

Popovich, R. P., et al., "Continuous Ambulatory Peritoneal Dialysis," *Annals of Internal Medicine*, 88(4):449–456, 1978.

Popovich, R. P. and Moncrief, J. W., "Mathematical modeling and minimum treatment requirements peritoneal dialysis," *Uremia, Pathobiology of Patients Treated for 10 Years or More, Proc. of the 3rd Capri Uremia Conf.*, 214–220, 1980.

Popovich, R. P. et al., "Transport Kinetics," *Peritoneal Dialysis*, 3rd Ed., Kluwer Academic Pub., 96–116, 1989.

Penzotti, S. C. and Mattocks, A. M., "Effects of Dwell Time, Volume of Dialysis Fluid, and Added Accelerators on Peritoneal Dialysis of Urea," *J. of Pharm. Sci.* 60:(10)1520–1522, 1971.

Pyle, W. K., "Mass Transfer in Peritoneal Dialysis," Ph.D Dissertation, Univ. of Texas, Austin, Texas, 1981.

Pyle, W. K., et al., "Peritoneal Transport Evaluation in CAPD" *CAPD Update, Continuous Ambulatory Peritoneal Dialysis*, Masson, N.Y., Chapter 7:35–52, 1981.

Raybuck, H. E. et al., "Absorption of serum from the peritoneal cavity, *Am. J. Physiol.* 199:1021–1024,1960.

Rubin, J., et al., "Drainage Volumes During Continuous Ambulatory Peritoneal Dialysis," *Am. Soc. Artif. Int. Organs*, 2(2):54–60, 1979.

(List continued on next page.)

OTHER PUBLICATIONS

Rubin, J., et al., "Peritonitis During Continuous Ambulatory Peritoneal Dialysis," *Annals of Intern. Med*, 92:7-13, 1980.

Rubin, J. et al., "Peritoneal dialysis during peritonitis," *Kid. Int.* 19:460-464, 1981.

Rubin, J., et al., "Protein Losses in Continuous Ambulatory Peritoneal Dialysis," *Naphron*, 28:218-221, 1981.

Rubin, J., et al., "Systems of membranes involved in peritoneal dialysis," *J. Lab. Clin. Invest.*, 110(4):448-453, 1987.

Sawada, et al., "Available Removal Systems: State of the Art," Therapeutic Hemapheresis in the 1990s. *Curr Stud. Hematol. Blood Transf.*, 57:51-113, 1990.

Schurig, R. et al., "Hemodynamic Studies in Long-Term Peritoneal Dialysis Patients," *Artificial Organs*, 3(3):215-218, 1979.

Stephen, R. L. et al., "Recirculating Peritoneal Dialysis with Subcutaneous Catheter," *Trans. Am. Soc. Artif. Intern Organs*, XXII:575-585, 1976.

Tsilibary, F. C. and Steven L. Wissig, "Absorption from the Peritoneal Cavity: SEM Study of the Mesothelium Covering the Peritoneal Surface of the Muscular Portion of the Diaphragm," *Am. J. of Anat.*, 149(1):127-133, 1977.

Tsilibary, F. C. and Wissig, S. L., "Light and Electron Microscope Observations of the Lymphatic Drainage Units of the Peritoneal Cavity of Rodenst," *Am. J. of Anat.*, 180:195-207, 1987.

Twardowski, Z. J., "New Approaches to Intermittent Peritoneal Dialysis Therapies," *Peritoneal Dialysis*, Third Edition, 133-151, 1989.

Urbaniak, S. J. and Robinson, E. A., "Therapeutic Apheresis," *British Med. J.*, 300:662-665, 1990.

Verger, C. et al., "Acute changes in peritoneal morphology and transport properties with infectious peritonitis and mechanical injury," *Kid. Int.*, 23:823-831, 1983.

Verger, C., "Peritoneal ultrastructure," *Peritoneal Dialysis*, 2nd Rev. Edition, Martinus Nijhoff Pub., 95-113, 1985.

Wayland, H., "Transmural and interstitial molecular transport," *Continuous Ambulatory Peritoneal Dialysis, Proc. of an Int'l., Symp.* Paris, Nov. 2 and 3, 1979, 18-27, 1980.

Zelman, A. et al., "Augmentation of Peritoneal Dialysis Efficiency with Programmed Hyper/Hypoosmotic Dialysates,", *Trans. Am. Soc. Artif. Intern. Organs*, XXIII:203-209.

Zong, M. et al., "A Serological Study of Hepatitis C Infection in Plasmapheresis Donors," *Chinese Med. J.*, 104(6):494-497, 1991.

ENHANCED PERITONEAL MEMBRANE PLASMAPHERESIS

BACKGROUND OF THE INVENTION

Field of the Invention

The presently claimed invention relates to apparatii and methods for enhancing the clinical efficacy of peritoneal membrane plasmapheresis (PMP) through optimization of sequential administration of vasoactive agents and solution osmolarities.

PMP Principles

PMP is a medical treatment for removing proteins from patients' blood while leaving formed elements (e.g., red and white cells) undisturbed. Systemic lupus erythematosus, myasthenia gravis, and Waldenström's macroglobulinemia are three examples of more than fifty diseases that can be effectively treated with PMP (Sawada et al. 1990). Treated patients show (generally temporary) clinical improvement when circulating levels of plasma proteins are reduced, and the treatment is usually repeated at intervals.

PMP is only one of several methods used clinically to reduce circulating blood protein levels. Another method, administration of corticosteroids, works on the principle that one may reduce blood protein levels by reducing blood protein production. A third commonly used method, based on removal of circulating plasma proteins, is called extracorporeal plasmapheresis (EP). Both steroid administration and EP, however, are associated with significant disadvantages when compared to PMP.

Disadvantages of steroid administration include the undesired side-effects (e.g., sodium retention, psychic derangements) often experienced by patients after treatment of even brief duration. EP, on the other hand, is complicated by the requirement to withdraw blood from the patient and separate it into plasma and formed elements. Though the process is relatively brief (compared to PMP), and formed elements are usually reinfused immediately in a protein-containing carrier fluid, EP is complex and costly (Hart et al. 1991). It is also subject to complications related to vascular access, infection, and possible contamination of the protein to be reinfused (Urbaniak et al. 1990; Malchesky et al. 1989; Zong-da et al. 1991).

Peritoneal Dialysis and PMP—Similarities and Differences

Dialysis is a method of separating crystalloids and colloids in solution by differences in their rates of diffusion through a semipermeable membrane (Agnew 1965). In peritoneal dialysis (PD), the membrane comprises the peritoneum and tissues which separate it from the circulating blood. Thus, the entire peritoneal cavity in PD acts as a temporary reservoir for dialysate, which is introduced and drained through a catheter placed through the abdominal wall. Several steps in the PD process are superficially similar to analogous steps in PMP, although the goal of PMP treatment, removal of plasma proteins, is substantially different from the object of PD therapy.

Some of PMP's advantages over other methods of removing plasma proteins stem from its resemblence to PD. PMP involves encouraging the passage of circulating proteins into the peritoneal cavity, from which they are relatively easily removed; as in PD, no transfer of blood outside the body is required. But unlike PD, protein passage across the peritoneum in PMP is primarily by convection (ultrafiltration), and only secondarily by diffusion. The creation of conditions favoring the preferred mode of protein passage in PMP is mediated by specific drug therapy.

Notwithstanding special drug requirements, however, typical conditions for PMP are similar in many respects to those for PD. For example, periodic treatment with either PMP or PD requires surgical implantation of a catheter to provide extracorporeal access to the peritoneal cavity. Other aspects of the treatments are also similar, including:

1. the infusion of an effective quantity of physiologic carrier fluid into the peritoneal cavity,
2. the retention of carrier fluid in the peritoneal cavity during a holding period, and
3. the subsequent drainage of carrier fluid from the cavity.

In PMP, however, the above steps are augmented by the concurrent addition of one or more vosoactive drugs to the infused solution, either as the fluid is being infused into the peritoneal cavity or during the holding period. Further, an anticoagulant may be required for PMP; it is usually given concurrently with the dialysate but is occasionally given subcutaneously, by mouth, or by intravascular infusion. If the latter method is chosen, administration may be intermittent.

PMP—Treatment Considerations

PMP avoids the risks of steroid administration; it removes more components (including proteins) from the plasma than dialysis and does so at less cost and risk than EP. But the amount of protein removed per unit time with PMP is generally less than that with EP, making it less preferred for some patients. The presently claimed invention overcomes this shortcoming of PMP by enhancing its protein removal rate. Thus, PMP is made more directly competitive with EP in a wide variety of clinical applications.

SUMMARY OF THE INVENTION

The presently claimed invention involves methods to nonselectively remove plasma proteins from the body at a rate comparable to conventional EP, but without the need for extracorporeal circulation of blood. The method extends the capabilities of PMP; hence the name: Enhanced PMP or EPMP. The nonselective nature of protein removal in EPMP may be effectively altered by selective reinfusion of removed proteins after extracorporeal separation of protein fractions.

EPMP is similar to PMP in that exogenous fluid is introduced through a catheter into the peritoneal cavity, held there for a period of time, then withdrawn. However, EPMP methods include the serial infusion and withdrawal of physiologic solutions which may contain vasodilator or vasoconstrictor drugs, or no vasoactive drugs. Solutions may be isotonic, hypertonic or hypotonic (relative to plasma) depending on whether the patient is desired to maintain fluid balance, lose fluid volume or gain fluid volume respectively. Use of hypertonic solutions generally results in an increase in the rate of protein removal.

Physiologic solutions in this context do not contain toxic concentrations of any substance, but their composition and tonicity may vary among those solutions known to those skilled in the art to be consistent with normal bodily function when used in the manner described herein.

Removal of plasma proteins during PMP and even PD is well-known in the prior art, though in the case of PD it is viewed as an incidental problem rather than a goal of therapy; protein losses during PD are clinically insignificant. For example, normal protein losses during continuous ambulatory peritoneal dialysis (CAPD) are approximately five to twenty grams per day in adults (Popovich et al. 1978). And even after a prolonged period in the peritoneal cavity, dialysate rarely contains more than 200 mg/dl of protein, or about 1/30th of the serum concentration (Rubin et al. 1981).

Consequently, the considerable literature on PD teaches little on the subject of protein losses generally and virtually nothing on methods for enhancing protein losses. Further, even though the effects of various vasoactive agents have been investigated in relation to PD (Maher et al. 1985) and PMP (Popovich et al. 1989), there is no prior art teaching on the alternating use of vasodilators and vasoconstrictors to enhance protein losses through the peritoneal membrane in PMP.

Daily Protein Removal with PD, PMP and EPMP

FIG. 1 represents experimental data showing serial daily protein removal rates in PD (Control Group), which are clinically insignificant. Much greater protein yields are obtained by the addition of a vasodilator to the PD solution, thus converting the method to PMP. But while PMP dramatically increases protein removal on the first day, protein yields on subsequent days are generally significally lower and more variable than first-day yields. A principal reason for this undesirable decline in protein removal efficiency is the appearance of local compensatory mechanisms in the peritoneal membrane and closely associated tissues after the first day of PMP. Such mechanisms decrease pore sizes with concomitant decrease in transfer of relatively large molecules (e.g., proteins), and the effects are not reversed by further treatment with a vasodilator. In the prior art, these refractory compensation effects have capped the maximum protein removal efficiencies of PMP protocols and therefore limited their clinical applicability.

In contrast, EPMP produces materially enhanced and unchanging daily rates of protein removal. The alternate inclusion of vasodilator and vasoconstrictor drugs in serial administrations of infused solution produces a surprising and unexpected result; it virtually eliminates the adverse effects of local tissue compensatory mechanisms on protein removal. Adaptations of this discovery to prior art methods featuring alternating hypotonic and hypertonic solutions yield the EPMP protocols used in the presently claimed invention.

BRIEF DESCRIPTION OF THE DRAWINGS

FIG. 12a—Volume profile of drained solution from the trial study of experiment PMP-10a.

FIG. 12b—Protein removal on an exchange basis from the trial study of experiment PMP-10a.

FIG. 13—Daily protein removal profiles of the trial study from experiment PMP-10a.

DESCRIPTION OF THE PREFERRED EMBODIMENTS

Figure 20:
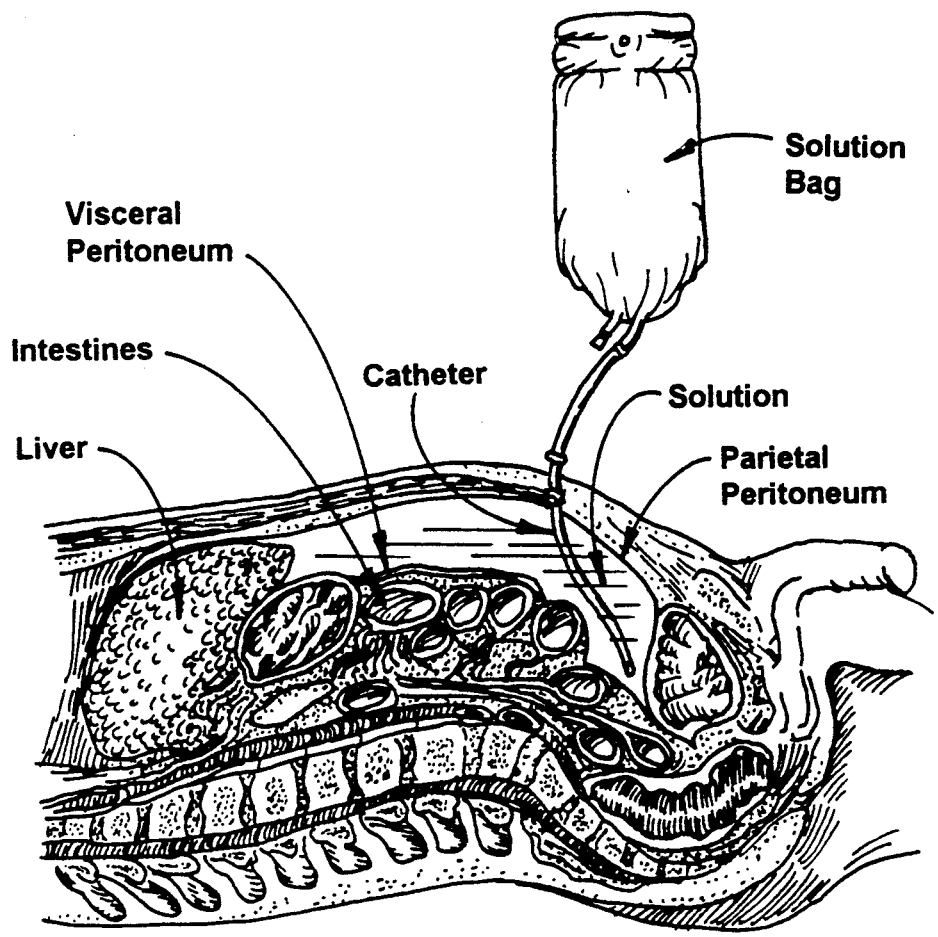
FIG. 20—Cross-section of the peritoneal membrane prepared for plasmapheresis.

The claimed invention is directed toward apparatii and methods of removing plasma components (preferably plasma proteins) from a patient's circulating blood across a serosal surface (primarily the visceral and parietal peritoneum) using alternating first and second solutions applied to the surface. In a preferred embodiment (see FIG. 20), a first solution containing a vasodilating drug is infused (instilled) into the patient's peritoneal cavity through an implanted peritoneal catheter. The first solution is allowed to remain in the peritoneal cavity for a first dwell time sufficient to effect removal of plasma components from the patient's circulating blood, after which the first solution is drained from the peritoneal cavity through the same or a different catheter. A second solution, containing a vasoconstricting drug, is then infused into the patient's peritoneal cavity in a similar manner; the solution is allowed to remain in the peritoneal cavity for a second dwell time. The second solution is then drained from the peritoneal cavity as the first solution was, and one returns to the step of infusing a first solution et seq. if removal of additional protein from the blood is desired. Alternate infusion methods as outlined by Miller (1966) and Twardowski (1989) can also be adapted to EPMP. Further, instilling and draining of either the first or second physiologic solution can be made to occur simultaneously by instilling through a first peritoneal catheter while draining through a second peritoneal catheter, said first and second catheters being implanted in the patient's peritoneal cavity in the manner indicated schematically in FIG. 20.

In another preferred embodiment, instilling and draining of the first solution may continue after the first dwell time and prior to any use of the second solution. After membrane pores are maximally or adequately opened by the vasodilator in the first solution, a third solution containing no vasoactive drug may be employed for serial instilling and draining (after a third dwell time) until the plasma protein removal rate declines below an acceptable value. At this time, local tissue compensation mechanisms leading to a reduced pore size may be reversed by instilling and draining the second solution (allowing a second dwell time in the peritoneal cavity). Thus, this embodiment retains the fundamental alternation of solutions containing vasodilator and vasoconstrictor, but allows flexibility in the number of times instillation/drainage cycles with any of the solutions can be repeated, and even allows the insertion of one or more instillation/drainage cycles with solution having no vasoactive drug (the third solution) if the maximal or otherwise desired level of drug effect has already been obtained by use of a prior (drug-containing) solution. Such drug effects would normally be estimated as at the desired level by observing that an effective amount of plasma protein is removed during draining.

In addition, the above embodiment includes the use of solutions of varying tonicity according to the needs of the patient. Considerations governing the choice of tonicity include the following:

1. If the patient is hypovolemic, administration of a hypotonic solution will tend to correct the hypovolemia through transfer of instilled fluid volume from the peritoneal cavity into the blood circulation. Note that hypovolemic patients may be treated simultaneously with EPMP and with separate administration of fluids (as by intravascular infusion), including plasma proteins and plasma expanders. Such administrations may be at any time, but are preferably done when the patient is asleep.
2. If the patient is hypervolemic, administration of a hypertonic solution will tend to correct the hypervolemia through transfer of circulating fluid volume from blood to the instilled fluid volume in the peritoneal cavity (with subsequent drainage of the instilled fluid volume).
3. If the patient is normovolemic, administration of a normotonic solution will tend to maintain normovolemia by minimizing net fluid movement across the peritoneal membrane in either direction.
4. In general, instillation of a hypertonic solution in the peritoneal cavity tends to increase the flow of fluid from the circulating blood, across the peritoneum, and into the instilled fluid volume within the peritoneal cavity. Subsequent drainage thus results in a relatively higher rate of plasma protein removal than would be expected with use of isotonic or hypotonic solutions.

It should also be noted that in addition to vasoactive drugs, any of the three solutions may contain plasma proteins intended for readministration to the patient. These proteins may be from sources other than the patient or may be the patient's own plasma proteins, from which the toxic or otherwise objectionable protein(s) have been separated by various means. One such separation means is extracorporeal protein fractionation, and another is the incorporation within one or more solutions of a specific adsorbent for each of the plasma proteins for which removal is desired.

In another preferred embodiment of the invention, one intermittently or continuously adds vasodilator drugs at intervals during the first dwell time, or intermittently or continuously adds vasoconstrictor drugs at intervals during the second dwell time.

The vasodilator drug may be dipyridamole, sodium nitroprusside, histamine phosphate or dibenzyline, but is not limited to these drugs. Those skilled in the art will recognize that a desired effect of the vasodilator drug is to increase the pore size of the peritoneal membrane and other tissues which separate the membrane from the circulating blood, thereby increasing the transport of plasma components from the circulating blood into the peritoneal cavity. The above listed drugs have this effect, and other drugs of the general class of vasodilators would be expected to have similarly beneficial effects.

The vasoconstrictor drug is preferably norepinephrine, but those skilled in the art will recognize that other drugs of the general class of vasoconstrictors may also have the desired effect of counteracting the physiologic compensatory mechanisms by which the transport of plasma components into the peritoneal cavity is reduced. The exact mechanisms are unclear, but the effect of vasoconstrictor in reversing them is demonstrated.

In preferred embodiments of the present invention, vasoconstrictor and vasodilator drugs are administered as components of the solutions and may reach their sites of action in the peritoneal membrane and associated tissues by direct contact, diffusion, or absorption into the systemic circulation. Those skilled in the art will recognize that the drugs may be administered by other routes (e.g., intravenously or intramuscularly) and still have the desired effects. Various modes of administration available to those skilled in the art (viz., bolus, drip, intermittent bolus) are thus included in the presently claimed invention. An anticoagulant may also be administered to the patient, and similar considerations apply to anticoagulants, which may be administered orally, intravenously (bolus, continuous or intermittent) or subcutaneously. Anticoagulant may also be added to the infused solution. In one preferred embodiment, the anticoagulant is heparin, but any anticoagulant having the desired effects of preventing occlusion of the catheter and preventing clotting from occurring in opened peritoneal pores may be used and is included in the claimed invention.

The first solution, with vasodilator, is preferably hypertonic, while the second solution, with vasoconstrictor, is preferably hypotonic (with respect to plasma). The degree of variation from isotonicity, as well as the dwell time each solution remains in the peritoneal cavity affects the amount of dehydration or rehydration which takes place with each solution. Thus, the degree of hypo- or hypertonicity may be chosen so as to restore or remove with the solution any desired amount of fluid after treatment is complete. In preferred embodiments of the invention, normal fluid balance of the patient is thereby preserved over the course of the treatment; it may also be replaced from other sources such as oral or intravenous fluid administrations.

Hypertonic peritoneal membrane plasmapheresis solutions tend to encourage movement of plasma components into the peritoneal cavity, so more hypertonic solutions are usually associated with increased rates of protein removal and dehydration. Additionally, most movement of plasma components into the peritoneal cavity occurs in the early portion of a dwell period. Hence, increasing the tonicity of the hypertonic solution and decreasing the dwell time (e.g., from about 4 to 8 hours, to about 0.5 to 1.5 hours) so as to have more frequent fluid changes tends to increase the total rate of protein removal.

Such accelerated rates of protein removal increase the desirability of removing certain proteins selectively and returning the remainder to the patient. This is easily accomplished as part of the current invention because drained solutions may be treated for selective absorption (removal) of some but not all proteins, after which the drained solution with some protein remaining is reinfused or otherwise readministered to the patient. Current therapeutic apheresis technologies are striving for this selective removal of plasma proteins (Sawada et al. 1990).

In these systems, the plasma is first separated from the cellular elements of blood, the plasma is then secondarily treated to selectively remove toxic proteins, and the treated plasma is returned to the patient. The selective removal systems include (Swada et al. 1990): 1) cascade (double) filtration 2) cryofiltration (filtration at below physiological temperature), 3) thermofiltration (filtration above physiological temperature), 4) on-line sorption (including charcoal, anion-exchange resin, immunoadsorbent, protein A, Citem 10, dextran sulfate-cellulose, heparin agarose and other absorbents). These systems can be utilized in conjunction with PMP to selectively remove the toxic proteins from the solution exiting the peritoneal cavity. This solution (containing non-toxic protein) can then be reused for subsequent infusions.

The treated solution could also be concentrated by a membrane system which allows passage of water but not of proteins. The concentrated protein solution could then be directly reinfused into the patient intravenously or instilled within the peritoneal cavity following treatment. Subsequent absorption through the lymphatic system would return the nontoxic proteins to the patient. Alternatively, encapsulated absorbent (or other suitable forms of absorbent for selective protein removal) can be injected into the peritoneal cavity and subsequently drained.

Finally, the methods described above for opening pores in and increasing convection across the peritoneal membrane with alternating applications of solutions containing vasodilators and vasoconstrictors can be applied to open the pores of other biological membranes. The resulting open pores can facilitate transport of, for example, proteins and drugs across the membranes, and the membranes need only be accessible to the solutions and materials to be transported. One can use this method to penetrate tumors such as ovarian cancer, thus facilitating treatment of the tumor with methotrexate or other chemo-therapeutic agents. Similarly, the method can be used to facilitate convection of fluids and materials in them across the blood-brain barrier; those skilled in the art will recognize that the porosity of many biological membranes can be increased in analogous ways.

EXAMPLES

The following examples are presented to describe preferred embodiments and utilities of the present invention, and are not meant to limit the invention unless otherwise stated in the claims appended hereto. Taken together, the examples illustrate representative demonstrations of the best mode of implementing the invention as currently understood.

EXAMPLE 1

Experimental Plans and Procedures

The Experimental Plan for PMP

PMP generally involves a process of removing proteins from the blood vascular space through the peritoneal cavity. Protein removal through the peritoneal membrane can involve both of the following mass transfer mechanisms:

1. solute diffusion due to a plasma-intraperitoneal solution gradient; and
2. convection due to water movement out of plasma (Popovich et al. 1987).

These mechanisms are investigated through administration of vasoactive drugs (intravenously, subcutaneously, intramuscularly or through the PMP solutions), and through alteration of the solution osmolarity and exchange schedule. Through proper choice of solution osmolarity, as well as drugs, dosages and route(s) of administration, one may maximize clearance of large molecular weight proteins during PMP.

Such maximization can yield protein removal rates in PMP comparable to the levels attainable with the most aggressive EP treatment. Increases in the transport rate of protein, however, may require effectively dealing with fibrinogen and other clotting factors, as well as increasing the peritoneal blood flow rate. The latter effect, in turn, can enhance the convection mechanism of protein transfer by allowing a higher volume of transperitoneal fluid shifts (ultrafiltration); such fluid shifts can drag (or convect) more protein molecules through the membrane.

PMP Experimental Protocols—General

The total of eleven clinical experiments is divided into three major groups. Group I includes PMP-1 (Francis, Jan. 19-Mar. 17, 1989); PMP-2 (Hi]de, Mar. 27-31, 1989); PMP-3 (Izzy, Apr. 24-28, 1989); PMP-4 (Georgia, May 10-19, 1989); and PMP-5 (Kit, Aug. 22, 1 989). Group II includes PMP-8 (May 14-17, 1990); PMP-9 (Sep. 10-21, 1990); PMP-10a (Samantha, Nov. 26-Dec. 4, 1990); PMP-10c (Samantha, Dec. 10-18, 1990); and PMP-11 (Tea, Dec. 12-20, 1990). Group III consists of PMP-10b (Samantha, Dec. 7, 1990).

Typical procedures for these experiments are as follows:

A) Standard peritoneal permeability study 1.5 Liter of 1.5% dialysate containing urea is infused into the peritoneal cavity of the canine by using a 14 gauge vascular needle below the umbilicus. Dialysate samples are obtained at 0, 10, 30, 60, 90 and 120 minutes.

B) Surgical implantation of the peritoneal catheter

1) After the standard peritoneal permeability study, a Moncrief-Popovich Swan Neck Catheter is implanted with sterile technique (Moncrief, J W et al., U.S. Pat. No. 5,057,075). A complete omentectomy and spay are performed at the same time. The bottom (coiled) tip of the catheter is placed at the lower portion of the peritoneal cavity, right above the bladder. The first Dacron (peritoneal) cuff of the catheter is introduced into the muscular layer next to the peritoneal membrane. The second Dacron (subcutaneous) cuff, which is located a few inches away from the peritoneal cuff as catheter turns around and makes an U curve, is implanted subcutaneously. The exit tip remains inside the subcutaneous layer at the end of this operation.

2) Intensive care is given for the next two days, 1 cc penicillin being injected daily. The whole catheter remains inside the canine body for at least three weeks for complete healing.

3) The design of the Moncrief-Popovich Catheter, coupled with the three week healing period, effectively prevents infection and leakage of intraperitoneal solution.

C) Control Study

1) The exit tip of the catheter is brought out of the skin using sterile technique. A titanium adapter and sterile tubing are attached to the catheter access tubing 2) 1.5 liter of 1.5% dextrose Dianeal ® dialysate solution is infused and immediately drained (a so called "wash out") three times (until the effluent becomes clear).

3) 1.5 Liter of 1.5% dextrose Dianeal ® dialysate is infused and remains inside the peritoneal cavity. Exchanges are made every 4 hours for 24 hours.

4) Serum protein samples are obtained at both the beginning and the end of the study. Dialysate samples are obtained following drainage at the end of every 4 hour period.

5) Protein electrophoresis or 24 hour urine protein tests are conducted in the lab of Austin Pathology Associates to determine protein concentrations.

6) The control study is omitted after PMP-1 and PMP-2. Data obtained from the control studies of PMP-1 and PMP-2 are considered as reference values for the rest of the experiments.

D) PMP Studies

In addition to the Control study, three different experimental protocols are investigated.

1) In group I (five canine studies), 4 mg histamine phosphate is added to 1.5 liters of 1.5% dextrose Dianeal ® every four hours. Because of the rapid drop off in protein removal rates, the alternating schedule (study group II) is initiated.

2) In group II (four canine studies), three one liter hypertonic exchanges, each containing 4 mg histamine phosphate, are alternated with three one liter hypotonic exchanges, each containing 1 mg norepinephrine, on a daily basis (4-hour dwell times).

3) Group III (one canine study) is similar to group II except that the residence (dwell) time is decreased to 1.5 hours with a total of six exchanges.

Summary of Materials and Methods

Mongrel research canines were purchased and implanted with Moncrief-Popovich catheters using standard procedures (Moncrief et al., 1991). A complete omentectomy and spay were performed. After a period of at least three weeks to allow complete complete tissue ingrowth into the implanted Dacron cuffs, the exit tip of the catheter was brought out of the skin and attached to sterile tubing via a titanium adapter. Three exchanges of 1.5 liters of Dianeal ® with 1.5% dextrose, Baxter Healthcare, Inc., Deerfield, Ill., were infused and immediately drained as a "washout". The hypertonic infusion solutions consisted of either 1.5% or 4.25% dextrose Dianeal ®, Baxter Healthcare, Inc., Deerfield, Ill., (346 or 485 mOsmol/l). The hypotonic solution consisted of 500 ml lactated Ringer's Inj., USP (273 mOsmol/l), and 500 ml 0.45% Sodium Chloride Inj. USP (155 mOsmol/l), Kendall McGraw, Irving, Calif. The vasodilator employed was histamine phosphate, Eli Lilly & Company, Indianapolis, Ind. The vasoconstrictor was Levophed ® (norepinephrine bitartrate), Winthrop Pharmaceuticals, New York, N.Y. Total protein was determined by the Cupric Biuret Reaction and Protein Electrophoresis by Beckman Instruments. Two-thousand five hundred units of Sodium Heparin, 1,000 USP units/ml, from LyphoMed Inc., Rosemont, Ill., were given subcutaneously two times daily with 1,500 units added to each 4.25% dextrose Dianeal ® solution.

EXAMPLE 2

Summary of Results

Figure 1:
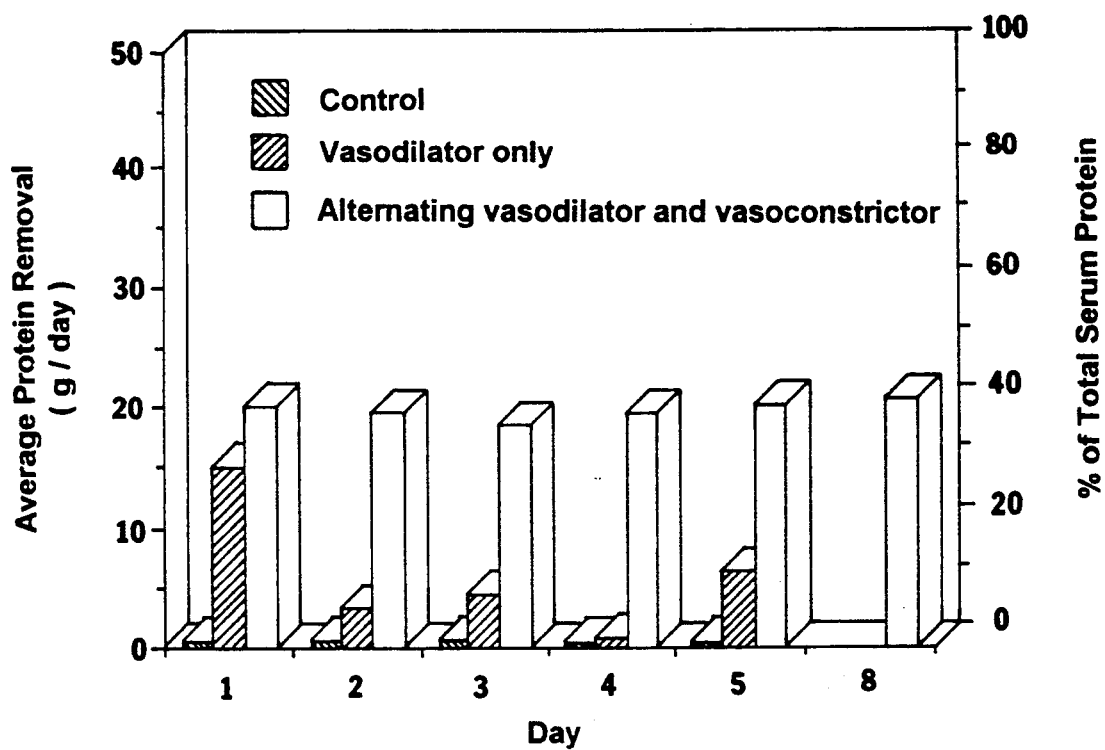
FIG. 1—Average protein removal rates and corresponding percent of total serum protein removed on a daily basis for controls and study groups I and II.

Average protein removal rates in grams per day and the corresponding average percent of the total serum protein removed per day are presented in FIG. 1 for the control group (standard CAPD protocol), study group I (vasodilator only) and study group II (alternating vasodilator/hypertonic and vasoconstrictor/hypotonic). Representative values (study group II) of the drained volumes and protein removal rates on an exchange-by-exchange basis are presented in FIGS. 18a and 18b.

Figure 3:
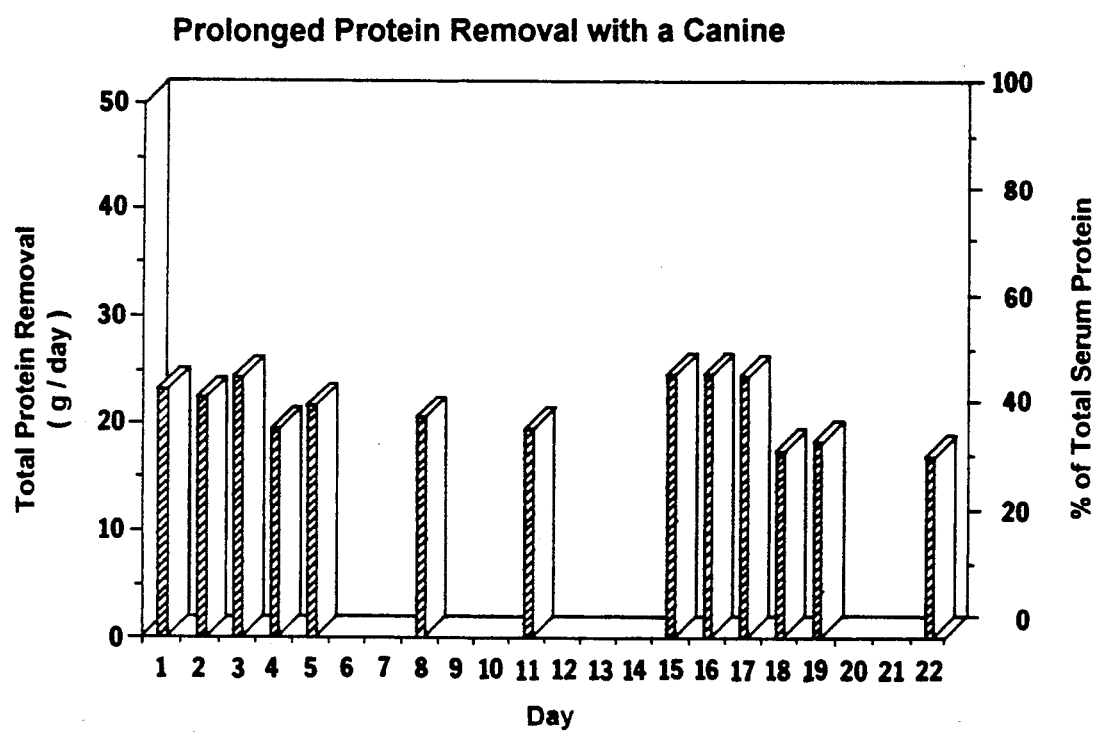
FIG. 3—Daily protein removal rates on a prolonged schedule with alternating solutions (hypertonic/-vasodilator and hypotonic/vasoconstrictor): PMP-10a (days 1-8), PMP-10b (day 11) and PMP-10c (days 15-22).
Figure 4:
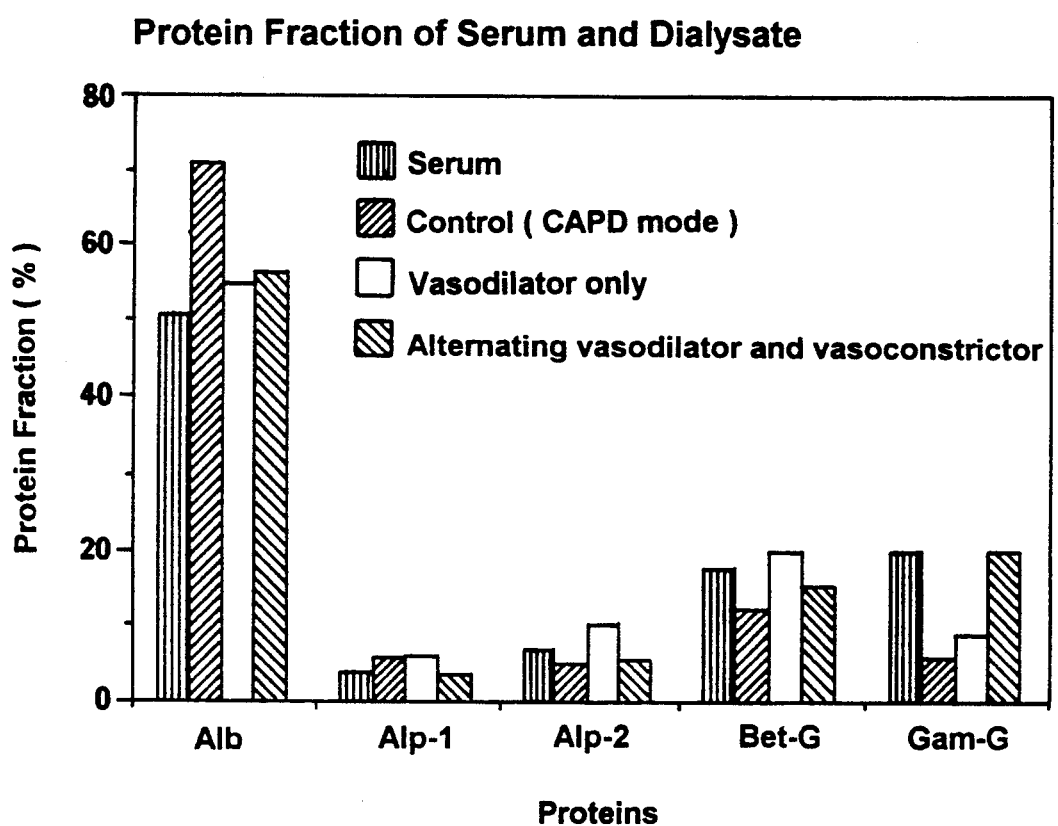
FIG. 4—Protein electrophoresis fractions for canine serum and drained solutions in controls and study groups I and II.

Daily protein removal rates and percent of total serum protein removed per day for a prolonged period (study group II) are illustrated in FIG. 3. The corresponding protein fractions for canine serum and protein in the drained solutions are illustrated in FIG. 4. Drained volumes and protein removal rates for study group III are presented in Table 7.

Mechanisms of Protein Transport

The transperitoneal concentration gradient is the driving force for solute transport in conventional peritoneal dialysis. Diffusion is the dominant factor in the mass transfer rate (Popovich et al., 1985). As illustrated in FIG. 1, very low protein removal rates are obtained in the control group (standard CAPD protocol) because of the low value of protein diffusion coefficients.

It is known that the addition of histamine phosphate to the infused solution can greatly increase protein transport (Popovich et al. (U.S. Patent), 1989). Histamine is a powerful dilator of the capillaries and a stimulator of gastric secretion. The osmotic pressure gradient caused by hypertonic dialysate solution, coupled with the hydrostatic intracapillary pressure, results in the convection of plasma through the pores into the peritoneal cavity. Thus, a convective rather than a diffusive mass transfer mechanism is employed. In study group I (vasodilator only), protein removal rates of 15 g/day (25% of total serum protein) are obtained for the first day of treatment. Thereafter, protein removal rates rapidly decline, despite the continued addition of histamine phosphate (FIG. 1). This may be caused by vasoactive compensation (e.g., the local release of vasoconstrictors to reestablish homeostasis), fibrinogen/fibrin occlusion, or other factors. Repeated applications of potent hypertonic solutions may also result in dehydration and consequent reduction in peritoneal blood flow.

The protein electrophoresis fractions for the various treatment modalities and canine serum are illustrated in FIG. 4. Note the relatively high proportion of albumin and low proportion of gamma-globulin for the CAPD control group. This suggests that classical concentration-driven diffusion is a significant mechanism in protein transport, since albumin has a higher diffusivity than gamma-globulin.

Conversely, the protein fraction for the alternating protocol (study group II) is nearly identical to that of canine serum. This is convincing evidence that convection is the dominant protein transport mechanism. This is the basis for selecting the term plasmapheresis for this process as opposed to dialysis, which connotates a diffusion driven system.

Improved Method of the Claimed Invention

The method of the presently claimed invention overcomes PMP's problems of decreasing protein removal rates with time and potential dehydration. Alternating infusions are employed, comprising a hypertonic solution containing a vasodilator and a hypotonic solution containing a vasoconstrictor. Norepinephrine (a hormone secreted by the adrenal medulla in response to splanchnic stimulation, stored in the chromaffin granules and released in response to hypotension) is selected as the vasoconstrictor for this preliminary study. It is used clinically as a sympathomimetic and pressor agent.

Alternating hypotonic/vasoconstrictor infusions are found to reduce local compensation or other factors to obviate the decrease in protein removal rates, and to partially restore the fluid ultrafiltered during the previous hypertonic exchange. Continuous, sustained protein removal rates (FIG. 1) average approximately 40% of the total serum protein in the canine per day. This is approximately equivalent to performing a conventional extracorporeal plasmapheresis treatment every other day with saline as the replacement fluid. Alternatively, it is noted that the first day resulted in substantial protein removal with the vasodilator only (FIG. 1). Thus, it is possible that either single or intermittent applications of the solution containing the vasoconstrictor would obviate the decrease in protein removal rates.

Figure 18A:
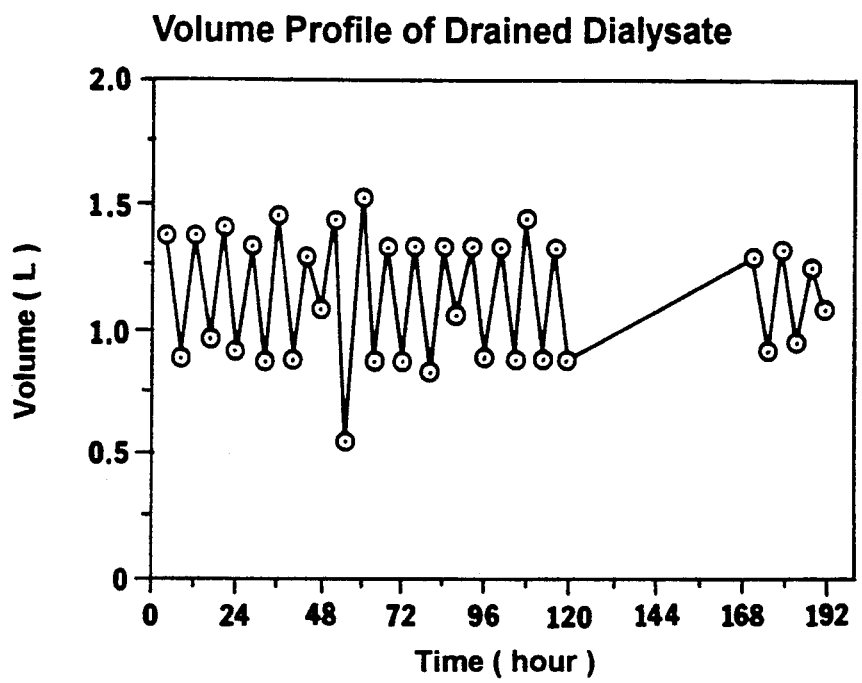
FIG. 18a—Volume profile of drained solution from the trial study of experiment PMP-11.
Figure 18B:
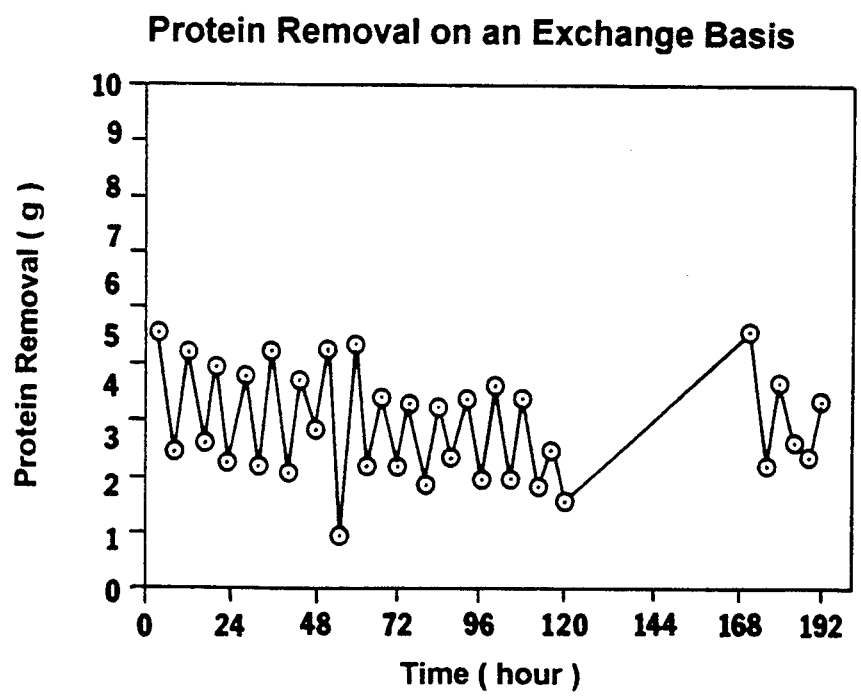
FIG. 18b—Protein removal on an exchange basis from the trial study of experiment PMP-11.

FIGS. 18a and 18b illustrate protein removal rates and drained volumes on an exchange basis for study group II (nominal one liter infusions). The drained volume after the four-hour dwell time for hypertonic solution with the vasodilator averages 1.36 liters, indicating a positive ultrafiltration of 0.36 liter per exchange. An average of 4.6 grams of protein is removed per exchange. The drained volume after the four-hour period of hypotonic solution with vasoconstrictive agent averages 0.90 liter, resulting in a negative ultrafiltration of 0.1 liter per exchange. An average of 3.14 grams of protein is removed per exchange: about ⅓ less than with the hypertonic exchanges. The tonicity of the infused fluids may be adjusted to achieve a zero net ultrafiltration rate.

This alternating PMP infusion methodology was conducted on a single canine subject for twenty-two days. The protein removal rates on a daily basis for these studies are illustrated in FIG. 3. Approximately 35% to 50% of the total plasma protein was removed on each of the thirteen days PMP was applied over the twenty-two day period.

Protein Replacement in PMP

During the experimental period, a science diet containing 225 gram protein/day is administered. The concentration level of total serum protein is 5.7 g/dl prior to the study. The total serum protein level is 5.4 g/dl on day eight and decreases to 3.8 g/dl on day twenty-two. After termination of the study, it rises at a rate of 0.5 g/day during the next two days. The canine subject exhibits normal healthy behavior throughout the experimental period with normal activity and appetite. The solutions drain readily and are clear throughout the studies, indicating the absence of either chemical or bacterial peritonitis. These results suggest that PMP may be used in prolonged clinical treatments without the additional intravenous infusion of replacement fluids or protein. Alternatively, plasma expanders may be administered (as, for example, intravenously) during the treatment (Moncrief, J W et al., The History and Current Status . . . , Table 2).

PMP with Reduced Solution Dwell Times

The rate of protein removal for study group III is presented in Table 1. The highest ultrafiltration occurs during the early phase of the solution dwell period with the 4.25% dextrose Dianeal ®, and reabsorption begins after four hours (Popovich, 1985). Thus, an even higher protein removal rate is obtained by reducing the dwell time from four hours to one and one-half hours. The total amount of protein removed is 19.6 grams over a treatment period of only nine hours. As illustrated in FIG. 3, this is comparable to the amount of protein removed in twenty-four hours during the group II (alternating schedule) studies. This raises the possibility of applying PMP over only a portion of the day, such as during sleeping hours, utilizing automated equipment in a manner analogous to automated peritoneal dialysis (Diaz-Buxo, 1985).

Vasoactive agents and cycling times are selected to yield protein removal rates comparable to the most aggressive EP treatments, but such an intensive approach may not be required. Since PMP can be applied on a daily (continuous) basis, satisfactory clinical results might be possible at significantly reduced protein removal rates if the objective is to maintain some toxic protein concentration below a critical level.

PMP Advantages Over EP

EP is an intermittent procedure. Toxic protein levels may rise following cessation of the treatment, in turn requiring very efficient intermittent treatments to maintain the concentration below a critical value during the inter-treatment period. A continuous procedure can have the same effect at a much lower efficiency. This is analogous to the difference between CAPD (a clearance of 8-10 ml/min applied continuously) and intermittent hemodialysis (a clearance of 150 ml/min applied for 4 hours, three times per week) which yields essentially the same maximum urea concentration levels. Thus, the continuous nature of PMP may afford a greatly reduced protein removal rate with reduced complications (including disequilibrium phenomena associated with intensive intermittent procedures) to achieve the same clinical results as the most aggressive intermittent extracorporeal plasmapheresis treatments. This would, of course, lower the quantity of vasoactive drugs required, along with their concomitant side effects and the cost of the procedure.

Although conventional plasmapheresis is comparatively safe (a mortality rate of about one per 3,000 procedures) appreciable problems may occur (Urbaniak, et al., 1990). Achieving adequate vascular access can lead to hematoma, thrombosis, gangrene, artery perforation, and sepsis. Complications associated with replacement fluids include allergic reactions (including anaphylaxis), electrolyte imbalance, viral hepatitis, citrate toxicity, hemorrhage and bacterial infection. Procedural difficulties in addition to high cost and the requirement for complex equipment include hyper- and hypovolemia, mechanical hemolysis, air embolus, chills, rigors, nausea and cost. PMP obviates many of these problems; it represents a potentially inexpensive, safe, continuous/nightly home treatment modality for protein mediated diseases.

EXAMPLE 3

Experimental Protocols—Group I

In group 1 of trial studies (PMP-1, PMP-2, PMP-3, PMP-4 and PMP-5), the detailed protocols are as follows:

PMP-1

Trial study period: 2.5 days
Solution volume: 2 liter
Solution osmolarity: 1.5% dextrose (346 mOsmol/L)
Exchange schedule: 3 times/day
Histamine phosphate:
 4 mg/each solution, 3 times/day
  Total dosage: 12 mg/day
Heparin:
 1,500 u./each solution, 3 times/day
 2,000 u./i.v., 3 times/day
  Total dosage: 10,500 u./day
Sample taken: 3 times/day when solution exchanged
Canine weight: 43 lbs

PMP-2

Trial study period: 3.3 days
Solution volume: 1.5 liter
Solution osmolarity: 1.5% dextrose (346 mOsmol/L)
Exchange schedule: 2 times/day
Histamine phosphate:
 4 mg/each solution, 2 times/day
  Total dosage: 8 mg/day
Heparin:
 1,500 u./each solution, 2 times/day
 3,000 u./i.v., 2 times/day
  Total dosage: 9,000 u./day
Sample taken: 2 times/day when solution exchanged
Canine weight: 46 lbs

PMP-3

Trial study period: 4.5 days
Solution volume: 1.5 liter
Solution osmolarity: 1.5% dextrose (346 mOsmol/L)
Exchange schedule: End of every 4 hour, 6 times/day
Histamine phosphate:
 4 mg/each solution, 6 times/day
  Total dosage: 24 mg/day
Heparin:
 1,500 u./each solution, 6 times/day
 5,000 u./subcu., 2 times/day
  Total dosage: 19,000 u./day
Sample taken: 6 times/day when solution exchanged
Canine weight: 40 lbs

PMP-4

Trial study period: 10 day
Solution volume: 1.5 liter
Solution osmolarity: 1.5% dextrose (346 mOsmol/L)
Exchange schedule:
 1st–5th day: 1 times/day
 6th–10th day: 6 times/day
Histamine phosphate:
 1st–5th day: 8 mg/3 times/day
  Total dosage: 24 mg/day
 6th–10th day: 4 mg/each solution, 6 times/day
  Total dosage: 24 mg/day
Heparin:
 1st–5th day: 1,500 u./3 times/day; 5,000 u./subcu., 2 times/day
  Total dosage: 14,500 u./day
 6th–10th day: 1,500 u/each solution, 6 times/day; 2,500 u/subcu., 4 times/day
  Total dosage: 19,000 u/day
Sample taken:
 1st–5th day: 1 times/day when solution exchanged
 6th–10th day: 6 times/day when solution exchanged
Canine weight: 45 lbs

PMP-5

Trial study period: 1 days
Solution volume: 1.5 liter
Solution osmolarity: 1.5% dextrose (346 mOsmol/L)
Exchange schedule: End of every 4 hour, 6 times/day
Histamine phosphate:
 4 mg/each solution, 6 times/day
  Total dosage: 4 mg/day
Heparin: 1,500 u./each solution, 6 times/day; 2,500 u./subcu., 4 times/day
  Total dosage: 19,000 u./day
Sample taken: 6 times/day when solution exchanged
Canine weight: 47 lbs

EXAMPLE 4

Experimental Procedures and Protocols—Group II

In group II of trial studies (PMP-8, PMP-9, PMP-10a, PMP-10c and PMP-11), the procedures employed are as follows:

First, a hypertonic solution (1 liter of 4.25% dextrose, osmolarity 485 mOsmol/L) containing 4 mg of histamine phosphate and 1,500 u. of heparin is infused and then maintained inside the peritoneal cavity for a period of 4 hour.

Second, a hypotonic solution (0.5 liter of Ringer's solution mixed with 0.5 liter of 0.45% saline solution, osmolarity 214 mOsmol/L) containing 1 mg of norepinephrine is infused and then maintained inside the peritoneal cavity for another period of 4 hour.

The above alternating procedures are conducted continuously, making 6 exchanges a day, three with hypertonic solution and three with hypotonic solution.

a) In addition to these exchanges, 2,500 u. heparin is injected subcutaneously, 2 times/day.

b) The total dosage of medications per day is: 12 mg of histamine phosphate, 9,500 u. of heparin, 3 mg of norepinephrine.

c) Samples are taken every other exchange set, i.e., @4 hours and 8 hours, @20 hours and 24 hours, and @36 hours and 40 hours, etc.

d) The trial study period for both PMP-8 and PMP-9 is 3 days.

e) The trial study period for PMP-10a, PMP-10c and PMP-11 is 8 days, including 5 days of experiments, followed by 2 days of rest, and finally 1 more day of experiment.

f) The hypotonic solution in PMP-11 is 1 liter of 0.45% saline solution only, osmolarity 154 mOsmol/L.

g) The detailed protocols are as follows:

PMP-8

Trial study period: 3 days
*1st solution changes: Hypertonic solution with vasodilator
Solution volume: 1 liter
Solution osmolarity: 4.25% dextrose (485 mOsmol/L)
Histamine phosphate:
  4 mg/each solution, 3 times/day
    Total dosage: 12 mg/day
Heparin:
  1,500 u./each solution, 3 times/day
  2,500 u./subcu., 2 times/day
    Total dosage: 9,500 u./day
* 2nd solution changes: Hypotonic solution with vasoconstrictor
Solution volume: 1 liter, consists of:
  0.5 liter of Ringer solution
  0.5 liter of 0.45% Saline solution
Solution osmolarity:
  Ringer solution: 273 mOsmol/L
  0.45% Saline solution: 154 mOsmol/L
  Mean value: 214 mOsmol/L
Norepinephrine: 1 mg/each solution, 3 times/day
  Total dosage: 3 mg/day
Exchange schedule: Alternating 1st and 2nd procedures
  @End of every 4 hour, 6 times/day
Sample taken: Every other exchange set i.e.,
  @4 hour and 8 hour;
  @20 hour and 24 hour, and
  @36 hour and 40 hour, etc. when solution exchanged
Canine weight: 45 lbs

PMP-9

Trial study period: 3 days
* 1st solution changes: Hypertonic solution with vasodilator
solution volume: 1 liter
solution osmolarity: 4.25% dextrose (485 mOsmol/L)
Histamine phosphate:
  4 mg/each solution, 3 times/day
    Total dosage: 12 mg/day
Heparin:
  1,500 u./each solution, 3 times/day
  2,500 u./subcu., 2 times/day
    Total dosage: 9,500 u./day
* 2nd solution changes: Hypotonic solution with vasoconstrictor
Solution volume: liter, consists of:
  0.5 liter of Ringer solution
  0.5 liter of 0.45% Saline solution
Solution osmolarity:
  Ringer solution: 273 mOsmol/L
  0.45% Saline solution: 154 mOsmol/L
  Mean value: 214 mOsmol/L
Norepinephrine: 1 mg/each solution, 3 times/day
  Total dosage: 3 mg/day
Exchange schedule: Alternating 1st and 2nd procedures
  @End of every 4 hour, 6 times/day
Sample taken: Every other exchange set, i.e.,
  @4 hour and 8 hour;
  @20 hour and 24 hour, and
  @36 hour and 40 hour, etc. when solution exchanged
Canine weight: 45 lbs PMP-10a and PMP-10c Trial study period: 8 days, consists of:
  5 days of experiments, followed by
  2 days of rest, and finally
  1 more day of experiment
* 1st solution changes: Hypertonic solution with vasodilator
Solution volume: 1 liter
Solution osmolarity: 4.25% dextrose (485 mOsmol/L)
Histamine phosphate:
  4 mg/each solution, 3 times/day
    Total dosage: 12 mg/day
Heparin:
  1,500 u./each solution, 3 times/day
  2,500 u./subcu., 2 times/day
    Total dosage: 9,500 u./day
* 2nd solution changes: Hypotonic solution with vasoconstrictor
Solution volume: 1 liter, consists of:
  0.5 liter of Ringer solution
  0.5 liter of 0.45% Saline solution
Solution osmolarity:
  Ringer solution: 273 mOsmol/L
  0.45% Saline solution: 154 mOsmol/L
  Mean value: 2i4 mOsmol/L
Norepinephrine: 1 mg/each solution, 3 times/day
  Total dosage: 3 mg/day
Exchange schedule: Alternating 1st and 2nd procedures
  @End of every 4 hour, 6 times/day
Sample taken: Every other exchange set, i.e.,
  @4 hour and 8 hour;
  @20 hour and 24 hour, and
  @36 hour and 40 hour, etc. when solution exchanged
Canine weight: 45 lbs

PMP-11

Trial study period: 8 days
* 1st solution changes: Hypertonic solution with vasodilator
Solution volume: 1 liter
Solution osmolarity: 4.25% dextrose (485 mOsmol/L)
Histamine phosphate:
  4 mg/each solution, 3 times/day
    Total dosage: 12 mg/day
Heparin:
  1,500 u./each solution, 3 times/day
  2,500 u./subcu., 2 times/day
    Total dosage: 9,500 u./day
* 2nd solution changes: Hypotonic solution with vasoconstrictor
Solution volume: 1 liter
Solution osmolarity:
  0.45% Saline solution (154 mOsmol/L)
Norepinephrine:
  1 mg/each solution, 3 times/day
    Total dosage: 3 mg/day
Exchange schedule: Alternating 1st and 2nd procedures
  @End of every 4 hour, 6 times/day
Sample taken: Every other exchange set, i.e., @4 hour and 8 hour;
@20 hour and 24 hour, and
@36 hour and 40 hour, etc. when solution exchanged
Canine weight: 48 lbs

EXAMPLE 5

Experimental Procedures and Protocol—Group III

In group III (PMP-10b only), the procedure is basically the same as with group II except the following:
a) The trial study period is only 1 day.
b) The exchange schedule is every 1.5 hour, 6 times/day.
c) Samples are taken following drainage every 1.5 hour, 6 times/during the whole experimental period of 9 hours.
d) The detailed protocol is as following:

PMP-10b

Trial study period: 1 days
* 1st solution changes: Hypertonic solution with vasodilator
Solution volume: 1 liter
Solution osmolarity: 4.25% dextrose (485 mOsmol/L)
Histamine phosphate:
  4 mg/each solution 3 times/day
    Total dosage: 12 mg/day
Heparin:
  1,500 u./each solution, 3 times/day
  2,500 u./subcu., 2 times/day
    Total dosage: 9,500 u./day
* 2nd solution changes: Hypotonic solution with vasoconstrictor Solution volume: 1 liter, consists of:
  0.5 liter of Ringer solution
  0.5 liter of 0.45% Saline solution
Solution osmolarity:
  Ringer solution: 273 mOsmol/L
  0.45% Saline solution: 154 mOsmol/L
  Mean value: 214 mOsmol/L
Norepinephrine:
  1 mg/each solution, 3 times/day
    Total dosage: 3 mg/day
Exchange schedule: Alternating 1st and 2nd procedures
  @End of every 1.5 hour, 6 exchanges/whole period of 9 hours
Sample taken: 6 times/whole period of 9 hours when solution exchanged
Canine weight: 45 lbs

EXAMPLE 6

Experimental Data and Analysis

Data from the following studies are presented in Tables and Figures as indicated below.

Figure 5:
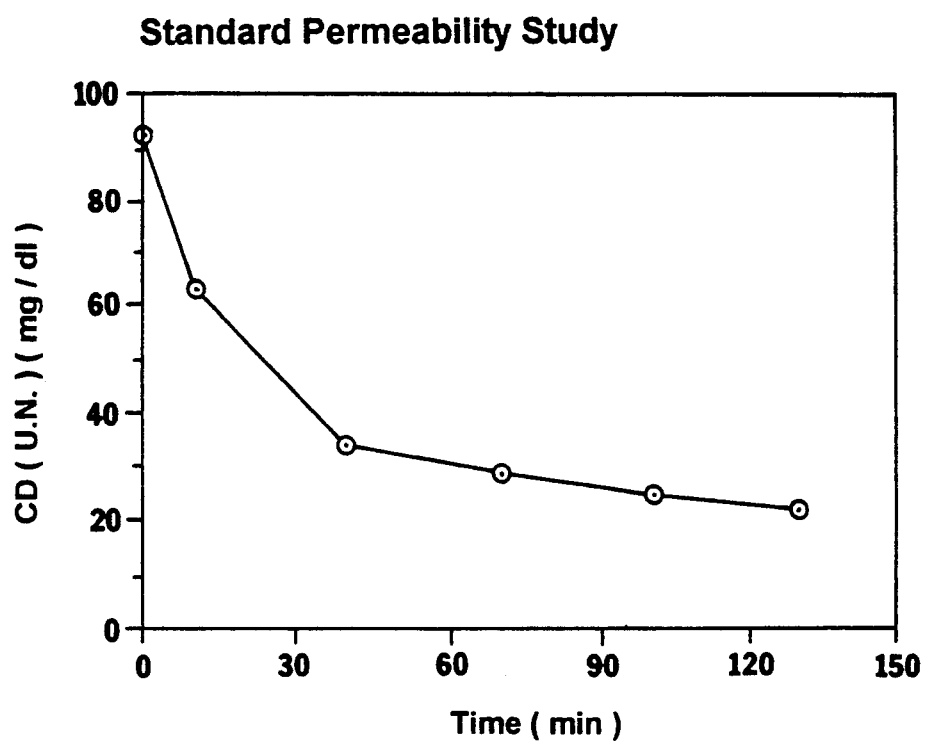
FIG. 5—Standard peritoneal permeability of urea-nitrogen, based on experiment PMP-1.
Figure 6:
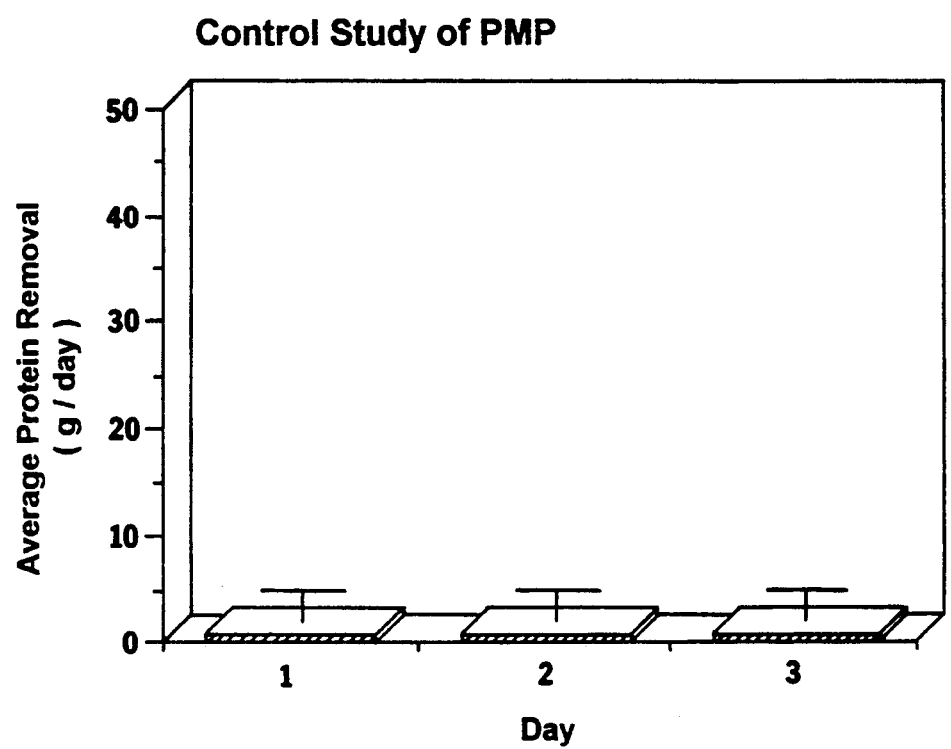
FIG. 6—Protein removal profile for PMP control study.
Figure 8A:
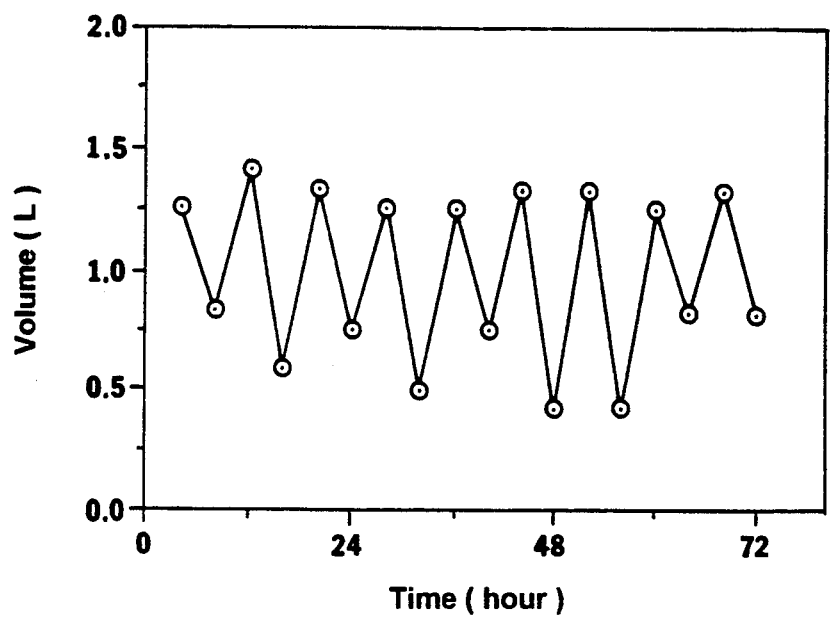
FIG. 8a—Volume profile of drained solution from experiment PMP-8.
Figure 8B:
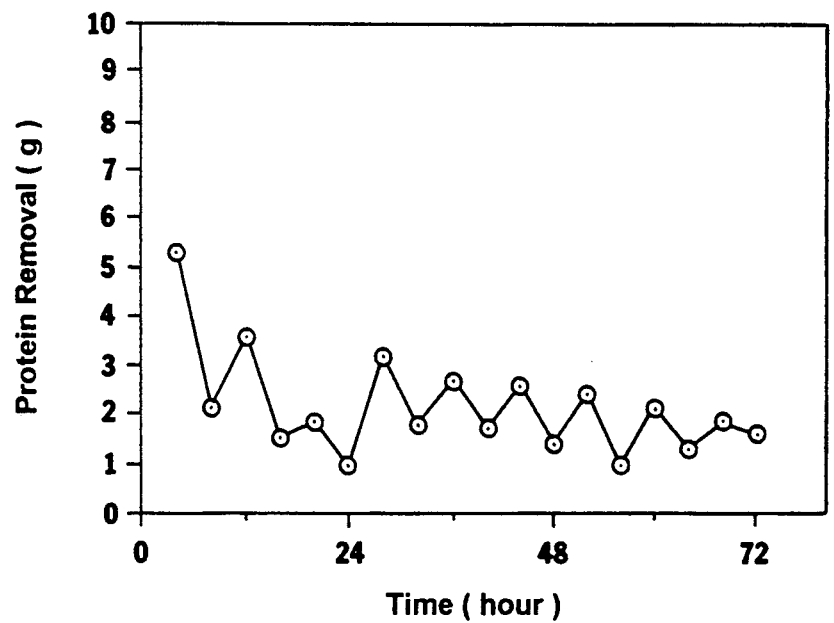
FIG. 8b—Protein removal on an exchange basis from experiment PMP-8.
Figure 9:
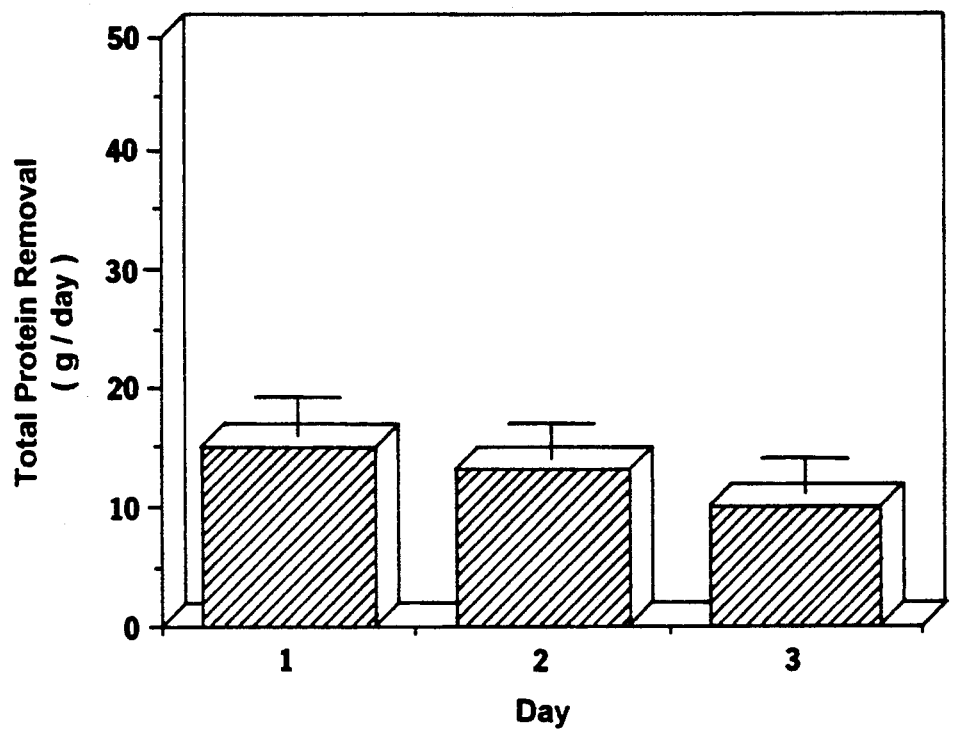
FIG. 9—Daily protein removal profiles of the trial study from experiment PMP-8.
Figure 10A:
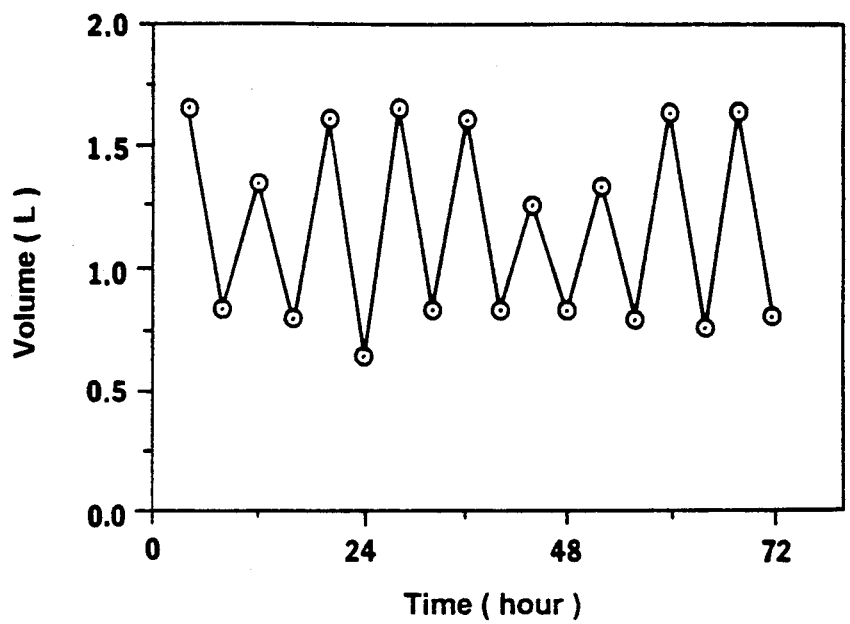
FIG. 10a—Volume profile of drained solution from the trial study of experiment PMP-9.
Figure 10B:
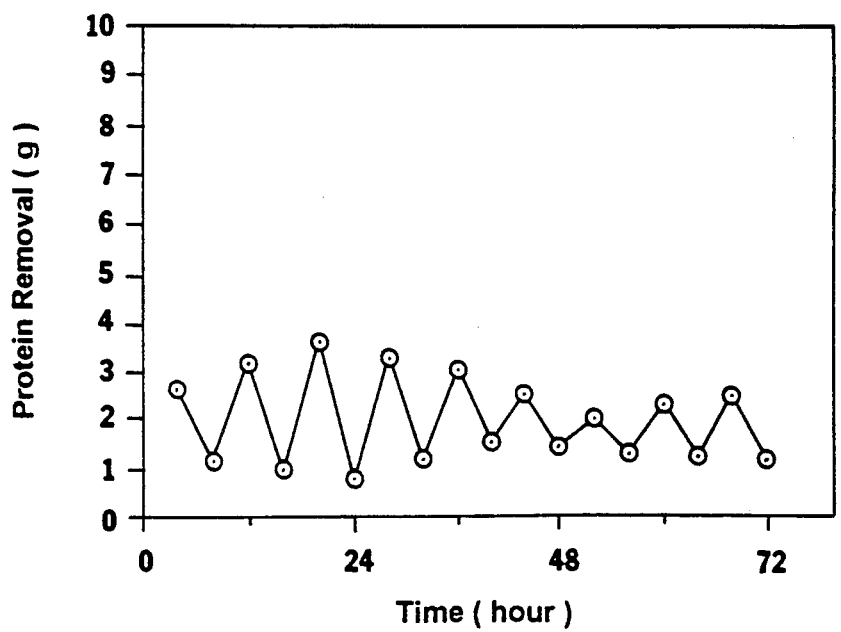
FIG. 10b—Protein removal on an exchange basis from the trial study of experiment PMP-9.
Figure 11:
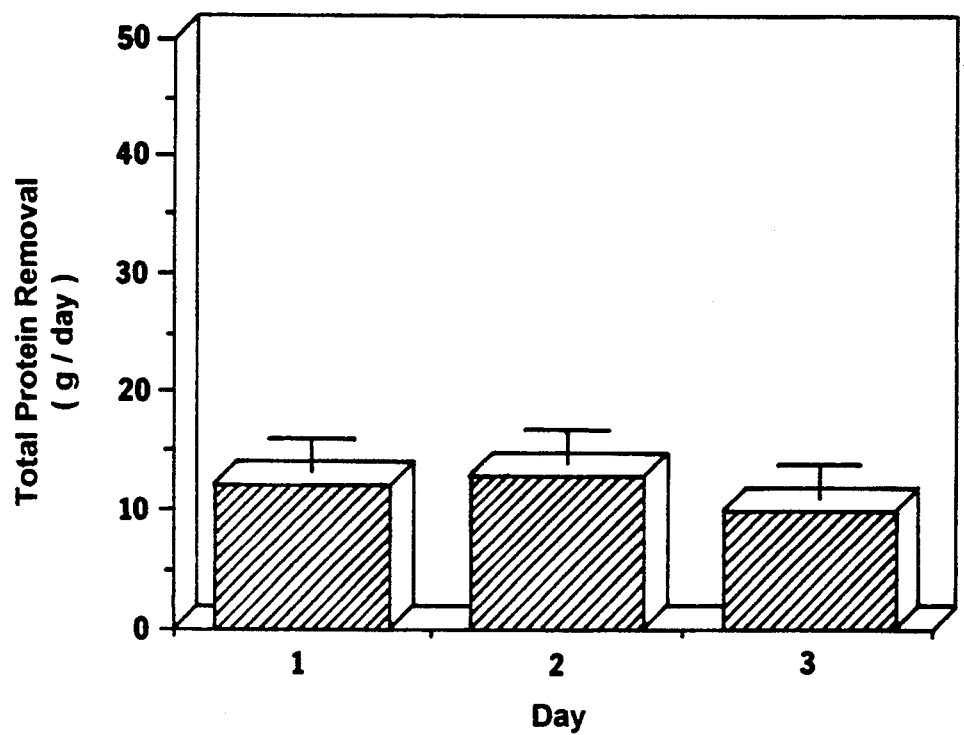
FIG. 11—Daily protein removal profiles of the trial study from experiment PMP-9.
Figure 12A:
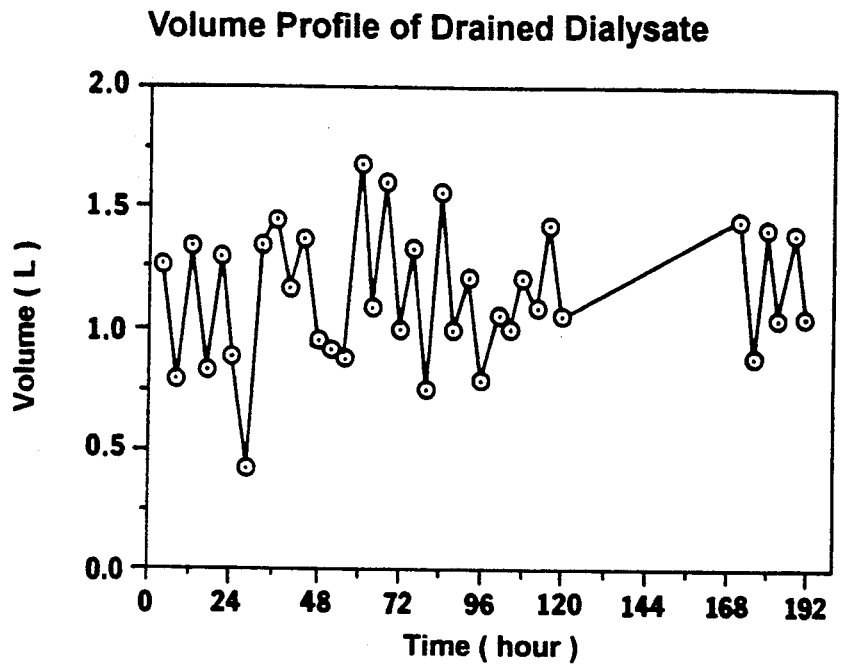
Figure 12B:
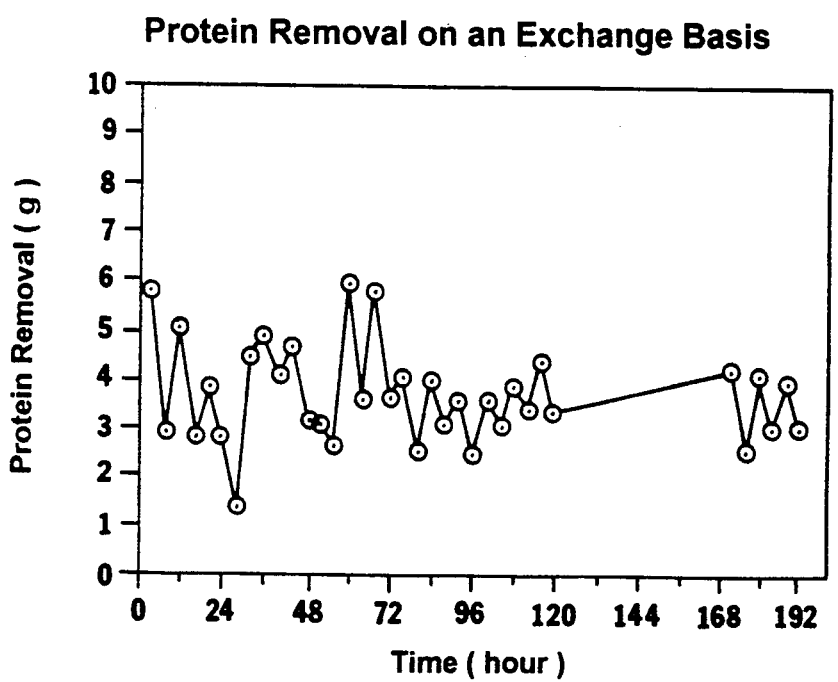
Figure 13:
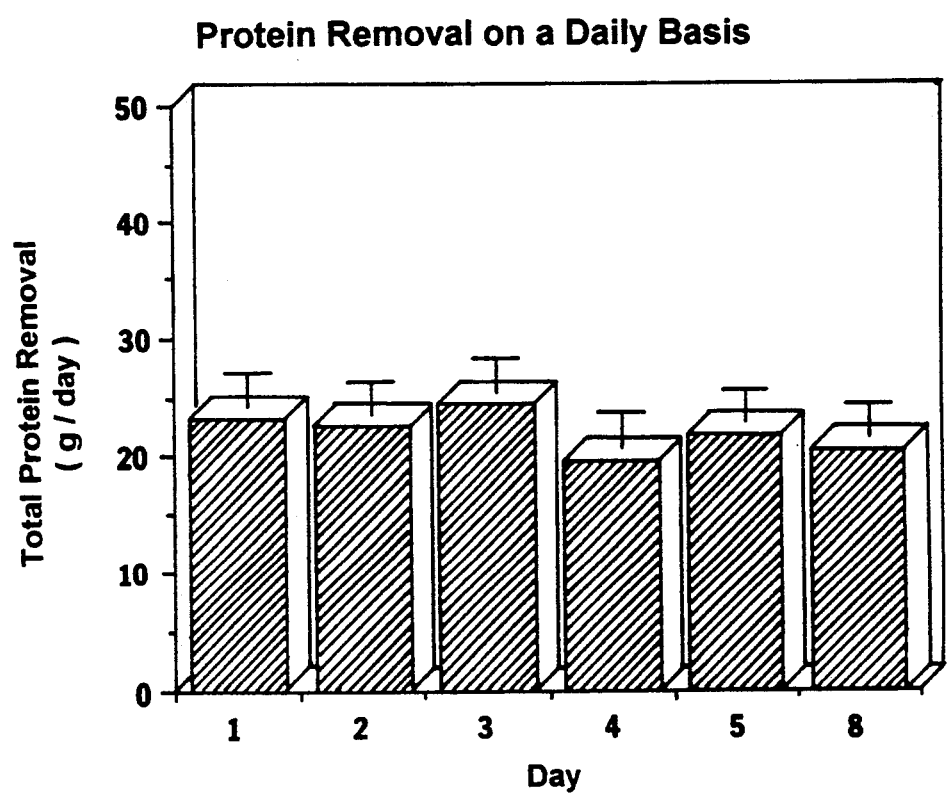
Figure 14A:
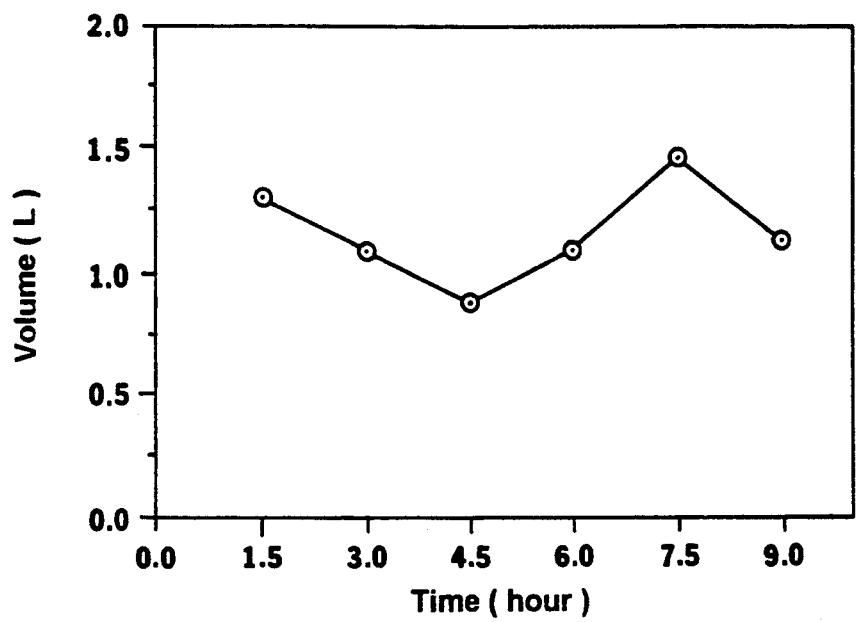
FIG. 14a—Volume profile of drained solution from the trial study of experiment PMP-10b.
Figure 14B:
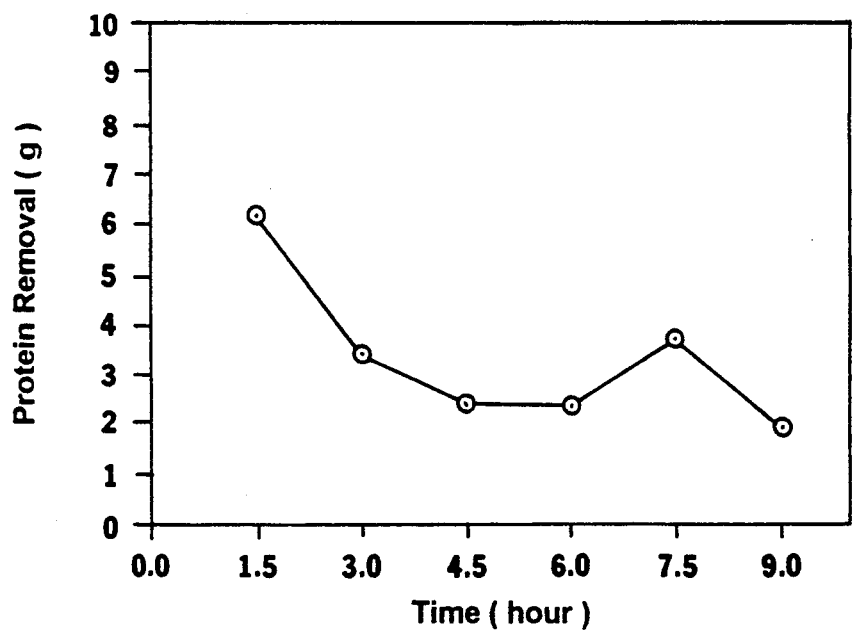
FIG. 14b—Protein removal on an exchange basis from the trial study of experiment PMP-10b.
Figure 15:
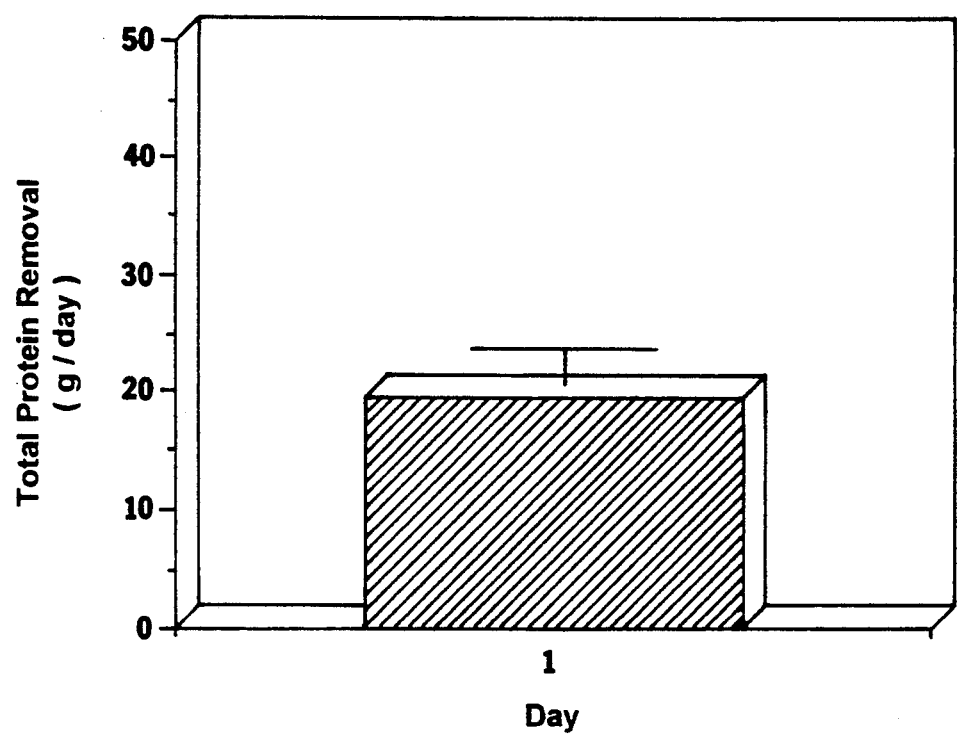
FIG. 15—Daily protein removal profiles of the trial study from experiment PMP-10b.
Figure 16A:
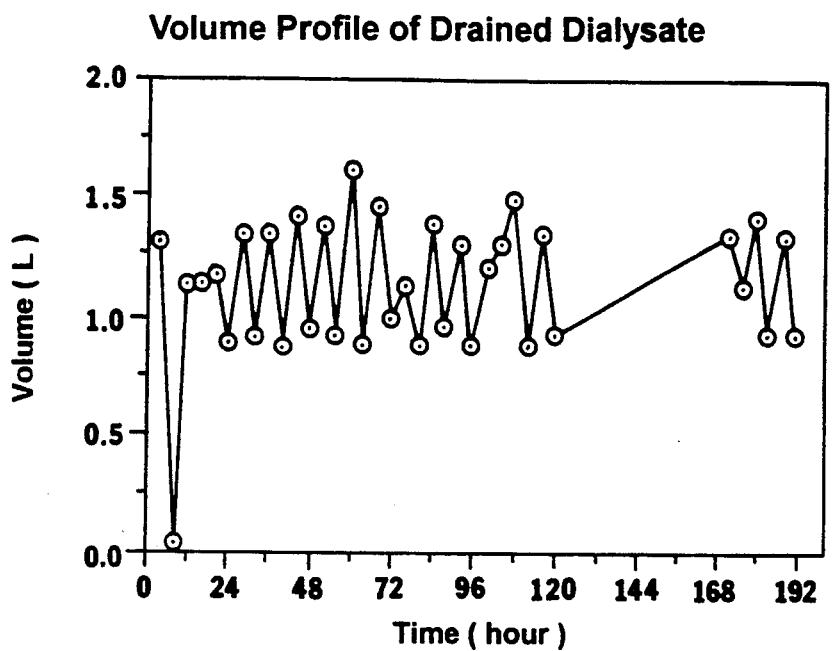
FIG. 16a—Volume profile of drained solution from the trial study of experiment PMP-10c.
Figure 16B:
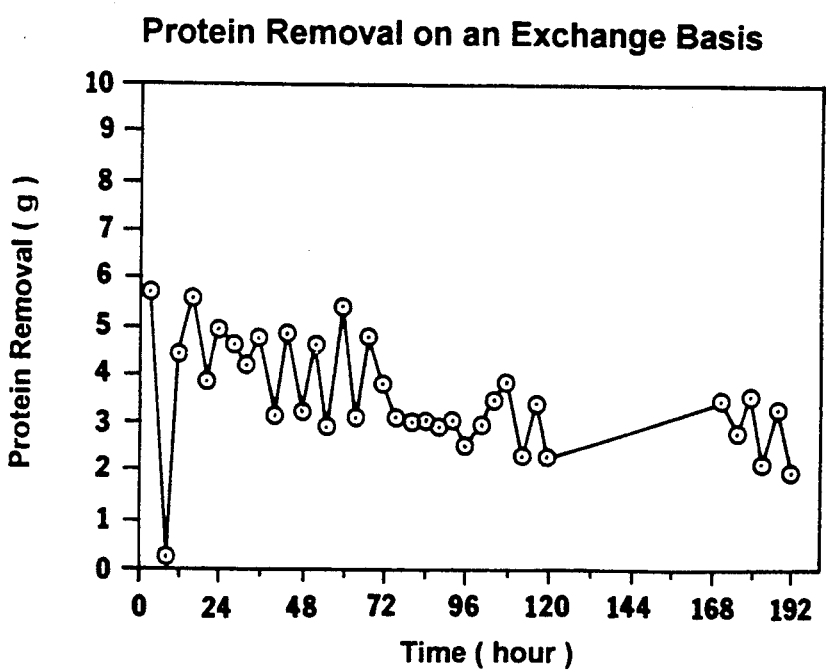
FIG. 16b—Protein removal on an exchange basis from the trial study of experiment PMP-10c.
Figure 17:
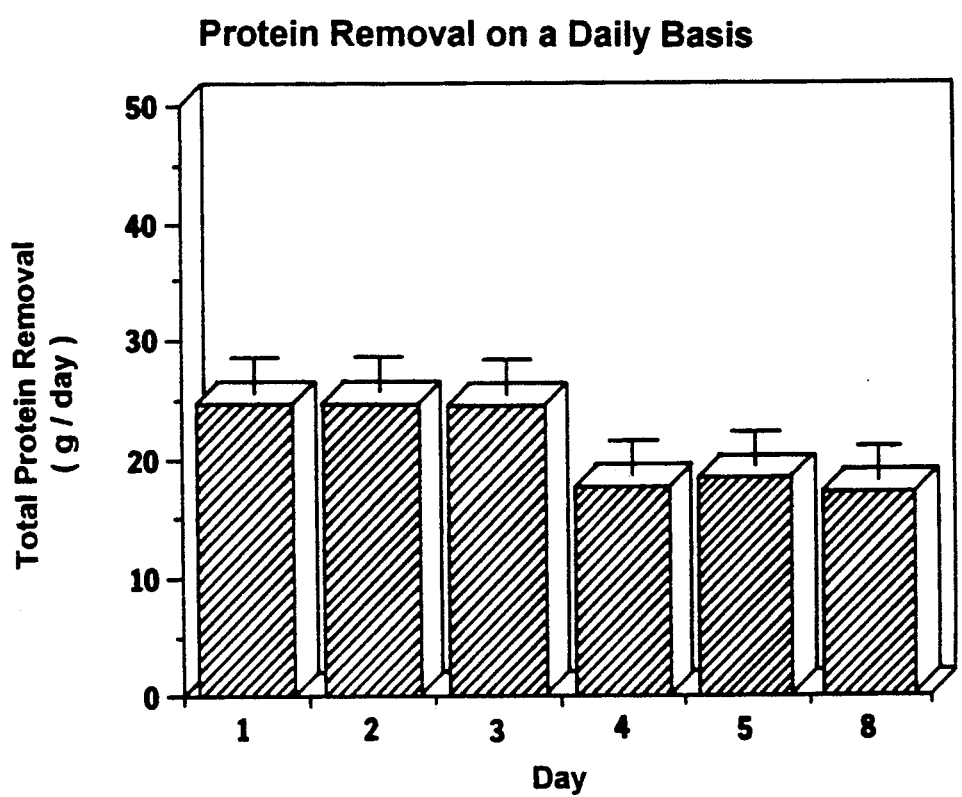
FIG. 17—Daily protein removal profiles of the trial study from experiment PMP-10c.
Figure 19:
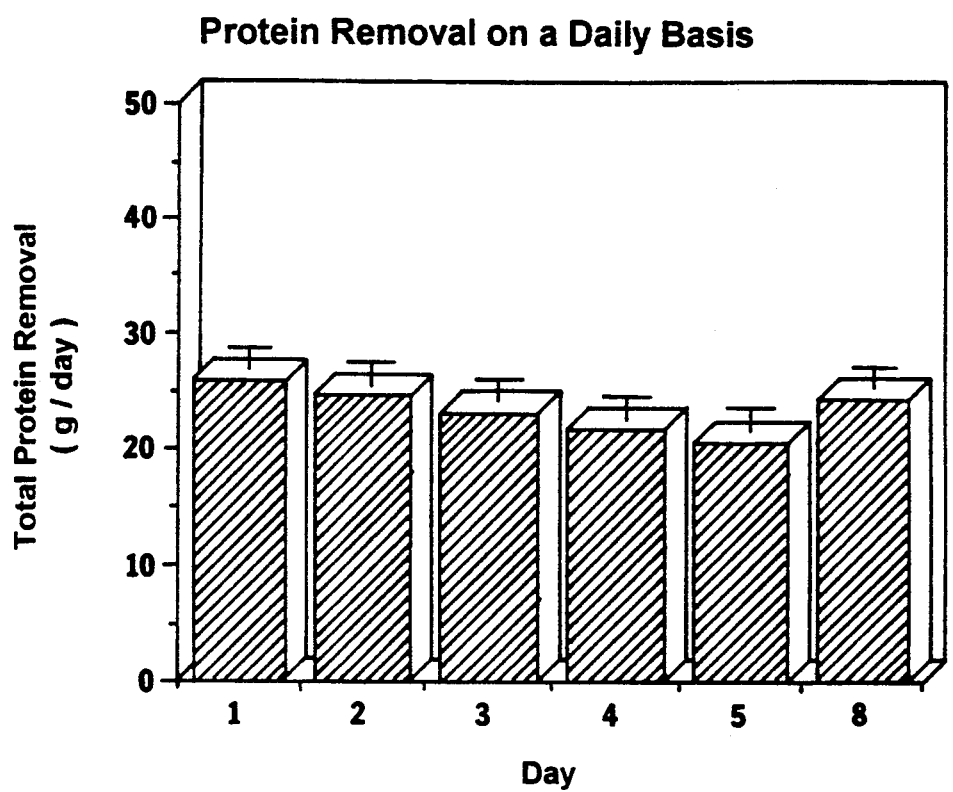
FIG. 19—Daily protein removal profiles of the trial study from experiment PMP-11.

Standard peritoneal permeability study of PMP-1: Table 1 and FIG. 5.
Control Study of PMP-1 and PMP-2: Table 2 and FIG. 6.
Trial Study of PMP-1 to PMP-5: Table 3 and FIG. 7.
Trial Study of PMP-8: Table 4 and FIGS. 8 and 9.
Trial Study of PMP-9: Table 5 and FIGS. 10 an 11.
Trial Study of PMP-10a: Table 6 and FIGS. 12 and 13.
Trial Study of PMP-10b: Table 7 and FIG. 14 and 15.
Trial Study of PMP-10c: Table 8 and FIG. 16 and 17.
Trial Study of PMP-11: Table 9 and FIG. 18 and 19.

TABLE 1

Standard Peritoneal Permeability Study from PMP-1

| Time (min) | Concentration of Urea-Nitrogen in Solution (mg/dl) |
|---|---|
| 0 | 92 |
| 10 | 63 |
| 40 | 34 |
| 70 | 29 |
| 100 | 25 |
| 130 | 22 |

TABLE 2

Average Daily Protein Removal
Control Study (Based on PMP-1 and PMP-2)

| | Daily Protein Removal (g/day) | | |
|---|---|---|---|
| Time (Day) | PMP-1 | PMP-2 | Average |
| 1 | 0.68 | 0.48 | 0.58 |
| 2 | 0.53 | | 0.53 |
| 3 | 0.52 | | 0.52 |
| Average | 0.58 | 0.48 | 0.54 |

TABLE 3

Average Daily Protein Removal
Trial Study from PMP-1 to PMP-5
(PMP-4a not used in the calculation of the Average)

| | Daily Protein Removal (g/day) | | | | | | |
|---|---|---|---|---|---|---|---|
| Day | PMP-1 | PMP-2 | PMP-3 | PMP-4a | PMP-4b | PMP-5 | Average |
| 1 | 6.91 | 9.40 | 46.53 | 0.53 | 6.60 | 6.77 | 15.24 |
| 2 | 7.40 | 2.61 | 1.08 | 0.53 | 1.42 | | 3.13* |
| 3 | 12.84 | 2.40 | 0.83 | 0.53 | 1.90 | | 4.49 |
| 4 | | 0.75 | 0.26 | 0.53 | 1.44 | | 0.82 |
| 5 | | | 10.58 | 0.53 | 1.96 | | 6.27 |
| Average | 9.05 | 3.79 | 11.86 | 0.53 | 2.66 | 6.77 | 5.98 |

TABLE 4

Trial Study from PMP-8

| Day | Hour | Drained Volume (L) | Protein Removal (g) | Total (g/day) |
|---|---|---|---|---|
| 1 | 4 | 1.25 | 5.29 | |
| | 8 | 0.83 | 2.09 | |
| | 12 | 1.41 | 3.56 | |
| | 16 | 0.58 | 1.51 | |
| | 20 | 1.33 | 1.82 | |
| | 24 | 0.75 | 0.92 | 15.20 |
| | 28 | 1.25 | 3.16 | |
| | 32 | 0.50 | 1.78 | |
| | 36 | 1.25 | 2.68 | |
| | 40 | 0.75 | 1.72 | |
| | 44 | 1.33 | 2.52 | |
| 2 | 48 | 0.42 | 1.34 | 13.20 |
| | 52 | 1.33 | 2.34 | |
| | 56 | 0.42 | 0.92 | |
| | 60 | 1.25 | 2.10 | |
| | 64 | 0.83 | 1.26 | |
| | 68 | 1.33 | 1.84 | |
| 3 | 72 | 0.83 | 1.56 | 10.06 |
| Average | | 0.98 | 2.13 | 12.82 |

TABLE 5

Trial Study from PMP-9.

| Time (Day) | Time (Hour) | Drained Volume (L) | Protein Removal (g) | Total (g/day) |
|---|---|---|---|---|
|   | 4  | 1.65 | 2.64 |   |
|   | 8  | 0.83 | 1.11 |   |
|   | 12 | 1.33 | 3.11 |   |
|   | 16 | 0.79 | 0.92 |   |
|   | 20 | 1.61 | 3.58 |   |
| 1 | 24 | 0.63 | 0.73 | 12.09 |
|   | 28 | 1.65 | 3.30 |   |
|   | 32 | 0.83 | 1.12 |   |
|   | 36 | 1.61 | 3.03 |   |
|   | 40 | 0.83 | 1.51 |   |
|   | 44 | 1.25 | 2.49 |   |
| 2 | 48 | 0.83 | 1.37 | 12.82 |
|   | 52 | 1.33 | 1.94 |   |
|   | 56 | 0.79 | 1.22 |   |
|   | 60 | 1.65 | 2.19 |   |
|   | 64 | 0.75 | 1.15 |   |
|   | 68 | 1.65 | 2.43 |   |
| 3 | 72 | 0.80 | 1.08 | 10.01 |
| Average |  | 1.16 | 1.94 | 11.64 |

TABLE 6

Trial Study from PMP-10a

| Day | Hour | Drained Volume (L) | Protein Removal (g) | Total (g/day) |
|---|---|---|---|---|
|   | 4  | 1.25 | 5.78 |   |
|   | 8  | 0.79 | 2.89 |   |
|   | 12 | 1.33 | 5.01 |   |
|   | 16 | 0.83 | 2.84 |   |
|   | 20 | 1.29 | 3.77 |   |
| 1 | 24 | 0.88 | 2.81 | 23.10 |
|   | 28 | 0.42 | 1.32 |   |
|   | 32 | 1.33 | 4.47 |   |
|   | 36 | 1.45 | 4.83 |   |
|   | 40 | 1.16 | 4.08 |   |
|   | 44 | 1.37 | 4.58 |   |
| 2 | 48 | 0.96 | 3.12 | 22.40 |
|   | 52 | 0.92 | 3.08 |   |
|   | 56 | 0.88 | 2.61 |   |
|   | 60 | 1.69 | 5.86 |   |
|   | 64 | 1.08 | 3.54 |   |
|   | 68 | 1.61 | 5.76 |   |
| 3 | 72 | 1.00 | 3.58 | 24.40 |
|   | 76 | 1.33 | 4.06 |   |
|   | 80 | 0.75 | 2.51 |   |
|   | 84 | 1.57 | 3.96 |   |
|   | 88 | 1.00 | 3.10 |   |
|   | 92 | 1.20 | 3.54 |   |
| 4 | 96 | 0.79 | 2.45 | 19.60 |
|   | 100 | 1.04 | 3.53 |   |
|   | 104 | 1.00 | 3.10 |   |
|   | 108 | 1.20 | 3.88 |   |
|   | 112 | 1.08 | 3.42 |   |
|   | 116 | 1.41 | 4.32 |   |
| 5 | 120 | 1.04 | 3.36 | 21.60 |
|   | 172 | 1.45 | 4.21 |   |
|   | 176 | 0.88 | 2.49 |   |
|   | 180 | 1.41 | 4.02 |   |
|   | 184 | 1.04 | 2.93 |   |
|   | 188 | 1.40 | 3.91 |   |
| 8 | 192 | 1.04 | 2.92 | 20.50 |
| Average |  | 1.13 | 3.66 | 21.93 |

TABLE 7

Trial Study from PMP-10b

| Hour | Drained Volume (L) | Protein Removal (g) | Total (g/day) |
|---|---|---|---|
| 1.5 | 1.29 | 6.16 |   |
| 3.0 | 1.08 | 3.32 |   |
| 4.5 | 0.88 | 2.33 |   |
| 6.0 | 1.08 | 2.27 |   |
| 7.5 | 1.45 | 3.63 |   |
| 9.0 | 1.12 | 1.86 | 19.60 |

TABLE 7-continued

Trial Study from PMP-10b

| Hour | Drained Volume (L) | Protein Removal (g) | Total (g/day) |
|---|---|---|---|
| Average | 1.15 | 3.26 | 19.60 |

TABLE 8

Trial Study from PMP-10c.

| Day | Hour | Drained Volume (L) | Protein Removal (g) | Total (g/day) |
|---|---|---|---|---|
|   | 4  | 1.29 | 5.67 |   |
|   | 8  | 0.04 | 0.18 |   |
|   | 12 | 1.12 | 4.38 |   |
|   | 16 | 1.12 | 5.56 |   |
|   | 20 | 1.16 | 3.86 |   |
| 1 | 24 | 0.88 | 4.91 | 24.60 |
|   | 28 | 1.33 | 4.58 |   |
|   | 32 | 0.92 | 4.19 |   |
|   | 36 | 1.33 | 4.70 |   |
|   | 40 | 0.88 | 3.11 |   |
|   | 44 | 1.41 | 4.84 |   |
| 2 | 48 | 0.96 | 3.19 | 24.60 |
|   | 52 | 1.37 | 4.56 |   |
|   | 56 | 0.92 | 2.87 |   |
|   | 60 | 1.61 | 5.33 |   |
|   | 64 | 0.88 | 3.04 |   |
|   | 68 | 1.45 | 4.78 |   |
| 3 | 72 | 1.00 | 3.78 | 24.40 |
|   | 76 | 1.12 | 3.08 |   |
|   | 80 | 0.88 | 2.99 |   |
|   | 84 | 1.37 | 3.02 |   |
|   | 88 | 0.96 | 2.89 |   |
|   | 92 | 1.29 | 3.01 |   |
| 4 | 96 | 0.88 | 2.52 | 17.50 |
|   | 100 | 1.20 | 2.96 |   |
|   | 104 | 1.29 | 3.49 |   |
|   | 108 | 1.49 | 3.78 |   |
|   | 112 | 0.88 | 2.28 |   |
|   | 116 | 1.33 | 3.47 |   |
| 5 | 120 | 0.92 | 2.27 | 18.30 |
|   | 172 | 1.33 | 3.37 |   |
|   | 176 | 1.12 | 2.75 |   |
|   | 180 | 1.41 | 3.53 |   |
|   | 184 | 0.92 | 2.12 |   |
|   | 188 | 1.33 | 3.08 |   |
| 8 | 192 | 0.92 | 1.98 | 17.00 |
| Average |  | 1.12 | 3.51 | 21.06 |

TABLE 9

Trial Study from PMP-11

| Day | Hour | Drained Volume (L) | Protein Removal (g) | Total (g/day) |
|---|---|---|---|---|
|   | 4  | 1.37 | 5.52 |   |
|   | 8  | 0.88 | 3.43 |   |
|   | 12 | 1.37 | 5.16 |   |
|   | 16 | 0.96 | 3.56 |   |
|   | 20 | 1.41 | 4.94 |   |
| 1 | 24 | 0.92 | 3.24 | 25.90 |
|   | 28 | 1.33 | 4.74 |   |
|   | 32 | 0.88 | 3.09 |   |
|   | 36 | 1.45 | 5.25 |   |
|   | 40 | 0.88 | 3.07 |   |
|   | 44 | 1.29 | 4.67 |   |
| 2 | 48 | 1.08 | 3.85 | 24.70 |
|   | 52 | 1.45 | 5.25 |   |
|   | 56 | 0.54 | 1.97 |   |
|   | 60 | 1.53 | 5.27 |   |
|   | 64 | 0.88 | 3.18 |   |
|   | 68 | 1.33 | 4.35 |   |
| 3 | 72 | 0.88 | 3.16 | 23.20 |
|   | 76 | 1.33 | 4.26 |   |
|   | 80 | 0.83 | 2.83 |   |
|   | 84 | 1.33 | 4.17 |   |
|   | 88 | 1.04 | 3.37 |   |
|   | 92 | 1.33 | 4.36 |   |
| 4 | 96 | 0.88 | 2.86 | 21.80 |
|   | 100 | 1.33 | 4.56 |   |

TABLE 9-continued

Trial Study from PMP-11

| Day | Hour | Drained Volume (L) | Protein Removal (g) | Total (g/day) |
|---|---|---|---|---|
|  | 104 | 0.88 | 2.88 |  |
|  | 108 | 1.45 | 4.38 |  |
|  | 112 | 0.88 | 2.76 |  |
|  | 116 | 1.33 | 3.48 |  |
| 5 | 120 | 0.88 | 2.54 | 20.60 |
|  | 172 | 1.29 | 5.55 |  |
|  | 176 | 0.92 | 3.14 |  |
|  | 180 | 1.33 | 4.62 |  |
|  | 184 | 0.96 | 3.54 |  |
|  | 188 | 1.25 | 3.32 |  |
| 8 | 192 | 1.08 | 4.27 | 24.40 |
| Average |  | 1.13 | 3.91 | 23.43 |

EXAMPLE 7

Analysis of PMP Studies

Protein Loss Factors in CAPD and PMP

Protein losses commonly occur during standard PD, but in the treatment of ESRD this has been viewed as a problem rather than part of the goal of therapy. Under normal circumstances, protein losses with CAPD are 5–12 grams/day in the human (Popovich, 1978). Even with long dwell exchanges, protein concentrations in the drainage rarely exceed 200 mg/dl or 1/30 of the serum concentration (Rubin, 1981 (Nephron)). Because of the extremely low diffusion rate of proteins across the peritoneum under standard dialysis conditions, the removal rate is clinically insignificant. It is far less than that which would be required to treat diseases being treated by conventional plasmapheresis.

In contrast to the standard CAPD treatment, the general goal of PMP is to maximize protein removal. Although protein clearance is not limited by solution flow rates and changes in the concentration gradient, previous studies have identified two factors which can increase protein transport. They are:
1) the use of hypertonic solution, which enhances protein removal by convection; and
2) vasodilator agents which increase peritoneum pore sizes.

Effects of Vasodilator on Protein Removal

Previous studies have shown that protein removal rates increase promptly after histamine phosphate is added as a vasodilator, but removal rates then decline within a few days despite the continued use of histamine phosphate. This may be caused by fibrinogen/fibrin occlusion on the vascular side of the peritoneum or by vasoactive compensation (e.g., the local release of endogenous vasoconstrictors to re-establish homeostasis). This effect is seen in data group I studies.

PMP Analysis Parameters

The clinical results discussed herein will be presented in terms of an equivalence index ($\Delta t$) based on the equation (1):

$$\Delta t = (V/V_D)(C/C_D)(t)(\Phi) \quad (1)$$

where
$\Delta t$ = time period between treatments in a conventional plasmapheresis [day]
V = protein volume of distribution [ml]
C = toxic protein concentration level [mg/dl]
$V_D$ = volume of drained solution [ml]
$C_D$ = toxic protein concentration level in drained solution [mg/dl]
t = dwell time for infused peritoneal solution [hours]
$\Phi$ = efficiency of plasmapheresis treatment This index ($\Delta t$) predicts the time between conventional plasmapheresis treatments which will yield the same maximum value of blood protein concentration level for a given set of PMP data.

The following values are assumed in the calculations:
C = 5.8 [g/dl] (total serum protein level)
V = 4% of the canine weight
$\Phi$ = 0.80 (i.e., 80% of circulating proteins are replaced by fresh plasma proteins during each standard plasmapheresis treatment)

Then, Equation (1) can be written in terms of only four variables to solve for $\Delta t$:

$$\Delta t = (7.73)(W)(t)(V_D/C_D) \quad (2)$$

where
$\Delta t$ = time period between treatments in conventional plasmapheresis [day]
W = canine weight [Kg]
t = dwell time for infused peritoneal solution [hour]
$V_D$ = volume of drained solution [L]
$C_D$ = protein concentration level in drained solution [mg/dl]

The average of these variables obtained from PMP studies, and the equivalence index $\Delta t$ calculated based upon them, are listed in Table 10.

The Control study data in Table 10 show that the standard CAPD technique is not suitable for plasmapheresis treatment. The protein removal rate (0.54 q/day) yields an equivalence index as high as 47 days. This means that it would take approximately 47 days of CAPD to obtain the same protein removal as that obtained in a single extracorporal plasmapheresis treatment.

TABLE 10

Average Variable Values and the Calculated Equivalence Index

| PMP No | Ave $V_D$ (L) | Ave $C_D$ (mg/dl) | Dwell (hour) | Weight (Kg) | Ave P.R. (g/day) | $\Delta t$ (day) |
|---|---|---|---|---|---|---|
| Control | 1.68 | 16 | 8 | 20.43 | 0.54 | 47.02 |
| 1st Group |  |  |  |  |  |  |
| 1 | 1.21 | 301 | 6 | 19.52 | 9.05 | 2.49 |
| 2 | 0.95 | 199 | 12 | 20.88 | 3.79 | 10.25 |
| 3 | 1.53 | 128 | 4 | 18.16 | 11.86 | 2.87 |
| 4 | 1.21 | 36 | 4 | 20.43 | 2.66 | 14.35 |
| 5 | 1.20 | 94 | 4 | 21.34 | 6.77 | 5.85 |
| Average |  |  |  |  |  | 7.16 |
| 2nd Group |  |  |  |  |  |  |
| 8 | 0.98 | 217 | 4 | 20.43 | 12.82 | 2.97 |
| 9 | 1.16 | 167 | 4 | 20.43 | 11.64 | 3.26 |
| 10a | 1.13 | 324 | 4 | 20.43 | 21.93 | 1.73 |
| 10c | 1.12 | 313 | 4 | 20.43 | 21.06 | 1.80 |
| 11 | 1.13 | 346 | 4 | 21.79 | 23.43 | 1.72 |
| Average |  |  |  |  |  | 2.29 |
| 3rd Group | 1.15 | 283 | 4 | 20.43 | 19.60 | 1.76 |
| 10b |  |  |  |  |  |  |

Group I Analysis

Figure 7:
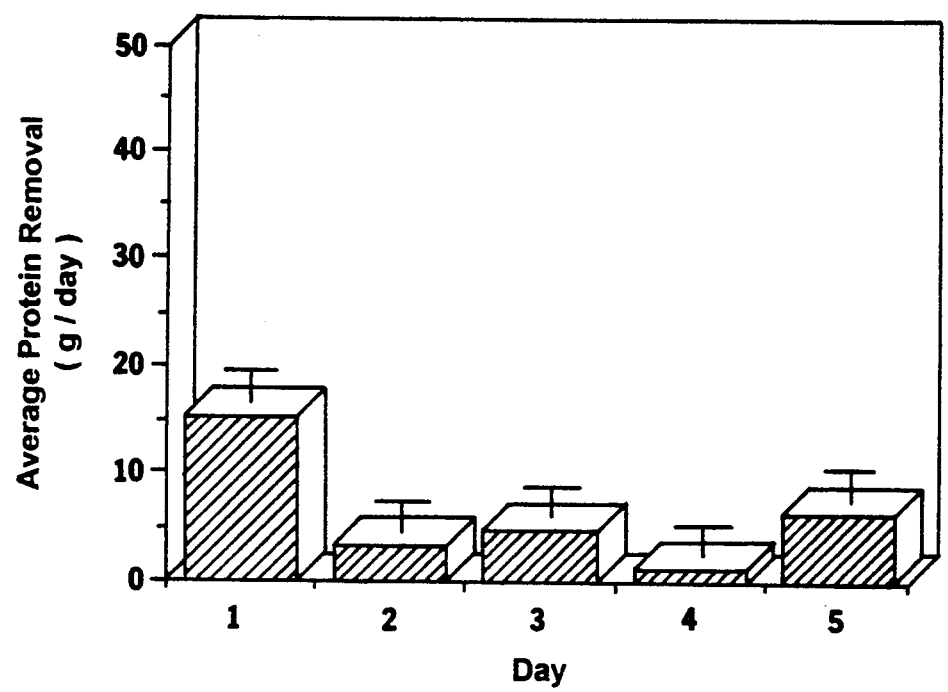
FIG. 7—Average daily protein removal profile of the trial study from experiments PMP-1 to PMP-5.

In group I (PMP-1 to PMP-5), various dosages of both histamine phosphate and heparin are used with different dwell times in an attempt to obtain adequate protein removal. Notwithstanding average daily protein removal rates more than 11 times that of the control study (5.98 g/day), however, the equivalence index is still higher than desired (average of 7.16 days). Also, as shown in FIG. 7, the protein removal rate decreases after the first day.

Mechanisms of Protein Transport

The transperitoneal concentration gradient is the dominant driving force of small solute transport in standard PD, and the mechanism of diffusion plays the major role in the net mass transfer rate (Nolph, 1989). Convection is an alternative mechanism for mass transport, particularly for large solutes. Net osmotic and hydrostatic forces promote the movement of water out of plasma and into the intraperitoneal fluid, and the transperitoneal fluid ultrafiltration convects protein molecules through the peritoneal membrane.

Based on group I PMP studies, it appears that peritoneal membrane porosity may be increased through pharmacological manipulations. Such an effect would certainly increase ultrafiltration under the influence of the hydrostatic pressure difference between the capillaries and the peritoneal cavity.

Hypertonic solutions may also be employed with short dwell times to produce substantially higher protein transfer rates than isotonic solutions (Pyle, 1981). Thus, ultrafiltration-induced convection (under the combined influence of hydrostatic and osmotic pressure), facilitated by pharmacologically-enhanced membrane porosity, would likely be the most beneficial transport mechanism for PMP.

Evidence for these mechanisms comes from electropheresis tests run in conjunction with the PMP-5 studies; in the tests, similar protein concentrations are found in the plasma and in the drained solution (Table 11 and FIG. 4). This indicates that large protein molecules are transported at nearly the same rate as the smaller ones, a situation which is not possible in a diffusion-dominant dialysis system in which smaller solutes transfer more rapidly than do larger ones.

In contrast, note that one does obtain a proportionately higher transport rate for albumin in the PMP Control (CAPD mode) studies. Clearly, then, while diffusion is an important mechanism in CAPD, the protein electropheresis results show that convection is the dominant mechanism for protein transport in PMP. This conclusion is also supported by the fact that histamine phosphate does not substantially increase urea transport (a diffusion-limited mechanism).

Further, as outlined in Table 11 and FIG. 4, the protein electropheresis pattern of PMP 8-10 is nearly identical to that of normal serum. Note that the high molecular weight solute $\gamma$ globulin has increase to a level found in canine plasma. These data also clearly illustrate that protein transport in PMP is dominated by convective transport with only minor effects from sieving and diffusion.

TABLE 11

Protein Fractions of Serum and Drained Peritoneal Solutions (*from [Handbook of Laboratory Animal Science])

| Protein | M.W. | Serum* | PMP-Control (CAPD) | PMP 1-5 | PMP 8-10 |
|---|---|---|---|---|---|
| Albumin | 69,000 | 51.1 | 71 | 55 | 56.0 |
| $\alpha_1$ Globulin | 44,000 | 4.1 | 6 | 6 | 3.4 |
| $\alpha_2$ Globulin | 54,000 | 7.2 | 5 | 10 | 5.3 |
| $\beta$ Globulin | 90,000 | 17.7 | 12 | 20 | 15.3 |
| $\gamma$ Globulin | 156,000 | 19.9 | 6 | 9 | 20.0 |
| Percentage | | 100% | 100% | 100% | 100% |

Group II Data Analysis

The data obtained from group II PMP studies demonstrate the beneficial effect of the presently claimed method on protein removal rates. As shown in FIGS. 8a, 10a, 12a, 14a, 16a and 18a, periodic volume changes occur in drained solutions. For example, in PMP-11 (see FIG. 18a), the drained volume of solution after the 4 hour dwell period for hypertonic/vasodilator solution averages 1.36 L, indicating a positive ultrafiltration of 0.36 L per exchange (see Table 9). Along with this high ultrafiltration rate, an average of 4.66 grams of protein per exchange is removed. On the other hand, the drained volume of solution after the 4 hour dwell period for hypotonic/vasoconstrictor solution averages 0.90 L, resulting in a negative ultrafiltration of 0.10 L per exchange. Along with this negative ultrafiltration rate, an average of 3.14 grams of protein per exchange was removed (about ¼ less than with hypertonic exchanges). Thus, the net volume change within the canine is only 0.26 L positive ultrafiltration for each dual exchange (1.36 L drained volume Versus 0.90 L drained volume). This difference is easily overcome by normal fluid intake or other means. PMP-11 data show an average of 3.91 grams of protein removal per exchange or 23.43 grams per day.

Note that in PMP-11, the average drained volume of solution after the 4 hour dwell period with hypotonic/vasoconstrictor solution is lower than in other studies (e.g., 0.90 L in PMP-11 versus 0.97 L in PMP-10a). This result demonstrates the effect of lowering the osmolarity of the hypotonic solution (154 mOsmol/L in PMP-11 versus 214 mOsmol/L in PMP-10a). The hypotonicity of the fluid can be further adjusted to obtain net fluid equilibrium with the alternating solutions, resulting in no net fluid loss to the patient.

As a general result, the average protein removal rate of the group II experiments (PMP-8 to PMP-11) is 19.74 g/day (see Table 12). This equals approximately ⅜ of the total plasma protein of 52 grams for the 20 Kg canine subject. The average removal rate of protein on a daily basis is illustrated in FIG. 1. Note the sustained high level of protein removal, and compare it to the control (CAPD) and PMP 1-5 studies. The equivalence index of these PMP studies averages 2.21 days (see Table 10).

Thus, if plasma proteins are continuously removed at this rate, it is equivalent to performing a conventional extracorporeal plasma exchange approximately every 2.21 days. This is equivalent to an aggressive plasmapheresis treatment and represents an effective clinical alternative treatment for numerous protein-mediated diseases.

Protein Replacement in PMP

Figure 2:
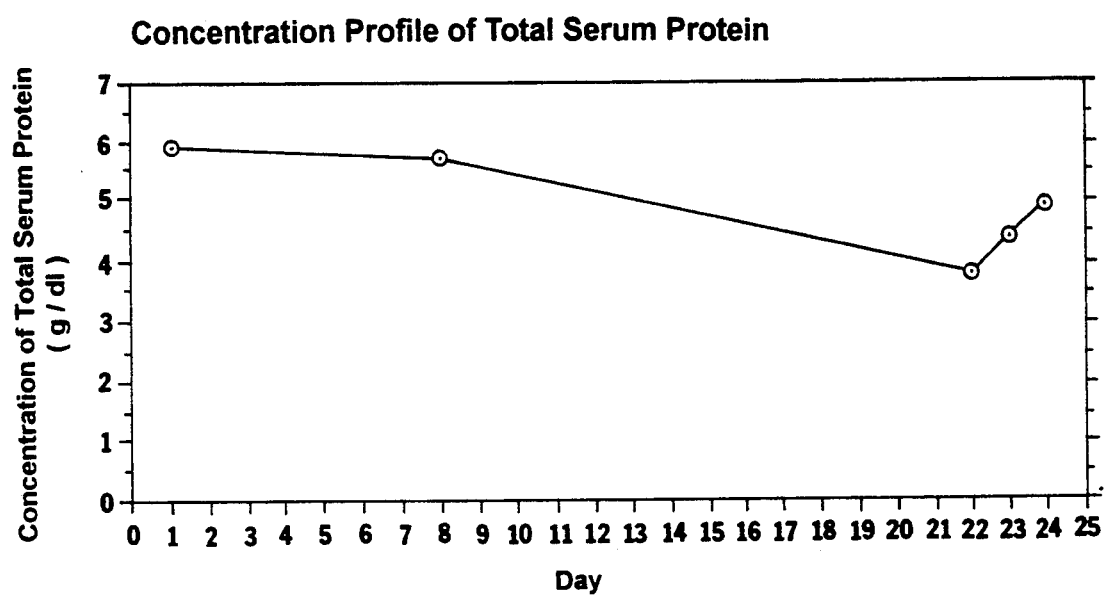
FIG. 2—Daily concentration profile of total serum protein on a prolonged PMP study: PMP-10a (days 1-8), PMP-10b (day 11) and PMP-10c (days 15-22).

The concentration level of total serum protein decreases with time during the PMP studies (e.g., 7.8 grams/dl prior to the PMP-11 study versus 5.6 grams/dl at the end of the 8th day of the study). However, the serum protein levels of the canine subject recovers quickly following the study. For example, the total serum protein level was 5.7 g/dl prior to the PMP-10 study. Notwithstanding a science diet containing 225 gram protein/day, the total serum protein level dropped to 3.8 g/dl after 22 days of experiments. Following the study, it rose at a rate of 0.5 g/day during the next two days (see FIG. 2). This suggests that the PMP procedure may be utilized in clinical treatments without the additional infusion of normal plasma proteins, making PMP less expensive than conventional extracorporal plasmapheresis in which plasma proteins are replaced.

TABLE 12

Data of Average Daily Protein Removal for Groups I and II

| Time (Day) | Average Daily Protein Removal (g/day) | |
|---|---|---|
| | 1st PMP Exp Group (PMP 1-5) | 2nd PMP Exp Group (PMP 8-11) |
| 1 | 15.24 | 20.06 |
| 2 | 3.13 | 19.54 |
| 3 | 4.49 | 18.44 |
| 4 | 0.82 | 19.63 |
| 5 | 6.27 | 20.16 |
| 8 | | 20.63 |
| Average | 5.98 | 19.74 |

Prolonged Protein Removal

Results of protein removal conducted on an intermittent basis on a single canine subject for 22 days (PMP-10a, b and c) are shown in FIG. 3. The canine subject exhibits normal healthy behavior throughout the experiments with normal activity and appetite. Clear dialysate drains readily throughout the studies, indicating the absence of either chemical or bacterial peritonitis. 35-50% of the total serum protein is removed each day PMP is applied over the 22 days, thus demonstrating the potential for prolonged PMP treatment.

Analysis of the Group III Study (PMP-10b)

In group III, PMP-10b illustrates the potential for further enhancement of protein removal. Based on the observation that the highest ultrafiltration occurs during the early portion of the dwell period with 4.25% dialysate, and reabsorption begins after 4 hours (Pyle, 1981), an even higher protein removal rate is obtained by reducing the dwell time (time between PMP exchanges) from 4 hours to 1.5 hours. Although there is a decreased protein removal on a per-exchange basis in PMP-10b, the total amount of protein removed over the experimental period of only 9 hours was 19.6 grams (see FIG. 15). If the protein removal rate of this 9 hour study were applied to the rest of the day, almost 2.5 times this amount of protein could be removed, leading to an equivalence index as low as 0.73 days. Of even greater significance, this raises the possibility of applying PMP over only a portion of the day, such as during the sleeping hours, utilizing automated equipment.

REFERENCES

The citations in the following list are incorporated in pertinent part herein for the reasons cited in the text.

Agnew, A et al.: *Dorland's Illustrated Medical Dictionary*, Saunders, Philadelphia:412 (1965).

Allen et al.: Role of fenestrated basement membrane in lymphatic absorption from peritoneal cavity. *Am J Physiol* 197:551-554 (1959).

Aune S: Transperitoneal exchange.III. The influence of transperitoneal fluid flux on the peritoneal plasma clearance of serum albumin in rabbits. *Scand J Gastroent* 5:105-113 (1970).

Babb, A. L, et al.: Bidirectional Permeability of the Human Peritoneum to Middle Molecules, *Proc. Eur. Dial. and Transpl Assoc.*:247 (1973).

Bambauer, R. et al.: Indications of plasmapheresis and selection of different substitution solutions. *Biomaterial Artificial Cells and Artificial Organs* 17(1):9-26 (1989).

Bird, RB, et al.: *Transport Phenomena*, John Wiley and Sons, New York, (1960).

Breborowicz, A, et al.: Augmentation of peritoneal dialysis clearance with procaine. *Kid Int* 26:392-396 (1984).

Breborowicz, A, et al.: Functional differentiation of rabbit peritoneum. Investigations in vitro. *Acta Med Pol* 25:1-5 (1984).

Breborowicz, A, et al.: Intracellular calcium ions modulate permeability of the peritoneal mesothelium in vivo. *Perit Dial Bull* 5(2):105-108 (1985).

Breborowicz, A, et al.: permeability of different parts of the peritoneal mesothelium to solutes: An in vitro study. *Per Dia Int* 9:135-141 (1989).

Brown, E A, et al.: Effects of hypertonic dialysate and vasodilators on peritoneal dialysis clearances in rats. *Kid Int* 13:271-277 (1978).

Chen, L T, et al.: *Chronic End-stage renal failure*. Heilongjang People's Press, 1-5 (1981).

Chou, C C, et al.: Physiological and pharmacological alternations in gastro-intestinal blood flow. In:Granger DN,Bulkley GB(eds), Measurements of Blood Flow: Applications to the splanchnic circulation. Williams and Wilkins, Baltimore, 477-509 (1981).

Clark, A J: Absorption from the peritoneal cavity. *J Pharm Exp Ther* 16:415-443 (1921).

Courtice, F C, et al.: The lymphatic drainage of plasma from the peritoneal cavity of the cat. *Austral J Exp Biol Med Sci* 28:161 (1950).

Diaz-Buxo J A: *Continuous cyclic peritoneal dialysis*, in Nolph KD(ed), Peritoneal Dialysis, Boston, Nijhoff Publishers, 247-266 (1985).

Drukker, W, et al.: *Replacement of renal functions by dialysis*, Maitinus Nijhoff (1978).

Flessner, M. F. et al.: Peritoneal lymphatic uptake of fibrinogen and erythrocytes in the rat. *Am J Physiol* 244:H89-H96 (1983).

Flessner, M. F. et al.: Exchange of micromolecules between peritoneal cavity and plasma. *Am J Physio* 248:H15-H25 (1985).

Ganter, G: Uber die Beseitigung giftiger Stoffe Aus dem Blut durch Dialyse. *Munch Med Wochschr* 70:1478-1480 (1923).

Goldberg, L I: Cardiovascular and renal actions of dopamine: potential clinical implications. *Pharmacol Rev* 24:1-30 (1972).

Goldschmidt, Z H, et al.: Effect of dialysate volume on peritoneal dialysis kinetics. *Kidney Int* 5:240-245 (1975).

Gosselin, R E, et al.: Diffusional transport of solutes through mesentery and peritoneum. *J Theor Biol* 3:487-495 (1962).

Granger, D N, et al.: Peritoneal dialysis solutions and feline splanchnic blood flow. *Clin Exp Pharmacol II:* 473-483 (1984).

Gray, H: *Anatomy of the Human Body*, 27th ed.C. Mayo(ed), Lea and Febiger, Philadelphia:1253-1272 (1959).

Gross, M, et al.: Effects of dialysate temperature and flow rate on peritoneal clearance. *JAMA* 202:363-365 (1967).

He Z: *Pharmacological enchancement of peritoneal mass transfer*. Austin, Tex., University of Texas, Ph. D. dissertation, 1991.

Hart, W, et al.: Estimating the cost of expanding an apheresis program. *Transfusions* 31:538-541 (1991).

Huang, Di, et al.: *Classic of internal medicine*, Press of People's Health. 503-547 (1963).

Henderson, L W, et al.: Altered permeability of peritoneal membrane after using hypertonic peritoneal dialysis fluid. *J Clin Invest* 48:992-1001 (1976).

Jihus, H, et al.: Clearance of diffusive substance of circulating blood by dialysis. *Trans Ass Am Physicians*, 28-51 (1913).

Kallen, R J: A method for approximating the efficacy of peritoneal dialysis for uremia. *Am J Dis Child* III:1-56-160 (1966).

Karnovsky, M J: The ultrastructural basis of capillary permeability studied with peroxides as a tracer. *J Cell Biol* 35:213-235 (1967).

Korthuis, R J: Role of the Peritoneal Microcirculation in Peritoneal Dialysis. *Peritoneal Dialysis*:28-47 (1989).

Leak, L V, et al.: Permeability of the diaphragmatic mesothelium: The ultra-structural basia for stomata. *Am J Anat* 151:557-579 (1978).

Legrain, M, et al.: *Place of chronic ambulatory peritoneal dialysis in the treatment of end stage renal failure, Continuous Ambulatory Peritoneal Dialysis*, Proceedings of an International Symposium, Paris, Nov. 2-3:3-47-353 (1979).

Lieb, W R, et al.: Biological membranes behave as non-porous polymeric sheets with respect to the diffusion of nonelectrolyte. *Nature* 224:240-243 (1969).

Mactier, R, et al.: Role of peritoneal cavity lymphatic absorption in peritoneal dialysis. *Kidney Int* 32: (1987).

Maher, J F, et al.: Isoproterenol enhancement of peritoneal permeability. *J Dial* 1:319-331 (1977).

Maher, J F, et al.: *Augmentation of Peritoneal Clearances by Drugs, Continuous Ambulatory Peritoneal Dialysis*, Proceedings of an International Symposium, Paris, Nov. 2-3:42-46 (1979).

Maher, J F: Peritoneal transport rates: Mechanisms, limitation and methods for augmentation. *Kid Int* 18:S117-S121 (1980).

Maher, J F, et al.: Pharmacological manipulation of peritoneal transport, in Nolph KD(ed), Peritoneal Dialysis, *Boston Nijhoff Publishers*, 267-296 (1985).

Malchesky, P S, et al.: Biomodulation effects of extracorporeal circulation in apheresis. *Seminars in Hematology* 26:42-51 (1989).

Miller, J H, et al.: Automated peritoneal dialysis: Analysis of several methods of peritoneal dialysis. *Trans Am Soc Artif Intern Organs* 12:98-105 (1966).

Miller, F N, et al.: Effects of peritoneal dialysis solutions on human clearances and rat arterioles. *Trans Am Soc Artif Intern Organs* 24:131-132 (1978).

Miller, F N, et al.: Microvascular and clinical effects of altered peritoneal dialysis solution. *Kid Int* 15:630-639 (1979).

Miller, F N, et al.: Hyperosmolality, acetate and lactate: Dilatory factors during peritoneal dialysis. *Kid Int* 20:397-402 (1981).

Miller, F N: *The peritoneal microcirculation*. In: Nolph KD(ed), Peritoneal dialysis, Martinus Nijhoff, Boston, 51-93 (1985).

Moncrief J W, et al.: *Method for implanting a catheter*. U.S. Pat. No. 5,057,075. Washington, DC, Patent and Trademark Office (1991).

Moncrief, J W, et al.: *Continuous Ambulatory Peritoneal Dialysis. Peritoneal Dialysis, Kluwer Academic Publishers*, 152-168 (1989).

Moncrief, J W, et al.: The History and current Status of Continuous Ambulatory Peritoneal Dialysis. *American Journal of Kidney Diseases*, XVI, (6):579-584 (1990).

Morgenstern, B Z, et al.: Convective characteristics of pediatric peritoneal dialysis, *Perit Dialysis Bull* 4:155-158 (1984).

Nagel, W, et al.: Study of the permeability of isolated dog mesentery. *Eur J Clin Invest*:149-154 (1970).

Nakamura, Y, et al.: Macromolecular transport in the cat mesentery. *Microvasc Res* 9:1-21 (1975).

Nolph, K D, et al.: Effects of intraperitoneal vasodilator on peritoneal clearances. *Dial Transpl* 7:812-817 (1978).

Nolph, K D, et al.: Determinants of low clearances of small solutes during peritoneal dialysis. *Kid Int* 13:1-17-123 (1978).

Nolph, K D, et al.: Effects of intraperitoneal nitroprusside in peritoneal clearances with variation in dose, frequency of administration, and dwell times *Nephron* 24 (1979).

Nolph, K D, et al.: Equilibration of peritoneal dialysis solutions during long dwell exchange. *J Lab Clin Med* 93:246-256 (1979).

Nolph, K D, et al.: *CAPD in chronic Renal Failure*, Brenner and Stein. Churchill Livingstone, N.Y., 197 (1981).

Nolph, K D, et al.: The Kinetics of ultrafiltration during peritoneal dialysis: The role of lymphatics. *Kidney Int* 32 (1987).

Nolph, K D, et al.: The Peritoneal Dialysis System. *Peritoneal Dialysis*:13-27 (1989).

Olin, T and Saldeen, T: The Lymphatic Pathways from the Peritoneal Cavity: a lymphangiographic study in the rat. *Cancer Res* 24:1700 (1964).

Popovich, et al.: *The genesis of the square meter-hour hypothesis*. Vol. XVII Trans Amer Soc Artif Int Organs, 1971.

Popovich, R P and Moncrief, J W: A model of the peritoneal dialysis system. *Proc 25th Ann Conf on Engr in Med And Biol* 14:172 (1976).

Popovich, R P, et al.: *Physiological Transport Parameters in Peritoneal and Hemodialysis*. 3rd Ann Rep No N01-AM-3-2205, AK-CUP, NIAMDD, NIH, Bethesda, Md. (1977).

Popovich, R P, et al.: Continuous ambulatory peritoneal dialysis. *Ann Intern Med* 88:449-456 (1978).

Popovich, R P, et al.: *Modeling and minimum treatment requirements peritoneal dialysis*. Proc 3rd Capri Conf on Chronic Uremia (1980).

Popovich, R P, et al.: *Peritoneal Membrane Plasmapheresis*, U.S. Pat. No. 4,673,385 (1987).

Popovich, R P, et al.: *Transport Kinetics. Peritoneal Dialysis*, 96-116, Kluwer Academic Publishers (1989).

Penzotti, S C, et al.: Effects of dwell time, volume of dialysis fluid, and added accelerators on peritoneal dialysis of urea. *J Pharm Sci* 60:1520-1522 (1971).

Pyle, W K, et al.: *Mass transfer in peritoneal dialysis*. Ph.D Dissertation, Univ. of Texas (1981).

Pyle, W K, et al.: *Mass transfer in peritoneal dialysis*. Masson NY: 32-52 (1981).

Raybuck, H E, et al.: Absorption of serum from the peritoneal cavity. *Am J Physiol* 199:1021 (1960).

Rubin, J, et al.: Drainage volumes during continuous ambulatory peritoneal dialysis. *Am Soc Artif Int Organs* 22:54-60 (1979).

Rubin J, et al.: Peritonitis during continuous ambulatory peritoneal dialysis. *Ann Intern Med* 92:7-13 (1980).

Rubin J, et al.: Peritoneal dialysis during peritonitis. *Kid Int* 19:460-464 (1981).

Rubin J, et al.: Protein losses in continuous ambulatory peritoneal dialysis. *Nephron* (1981).

Rubin J, et al.: Investigation of net sieving coefficient of the peritoneal membrane during peritoneal dialysis. *Am Soc Artif Intern Organs* J5:9–15 (1982).

Rubin J, et al.: Systems of membranes involved in peritoneal dialysis. *J Lab Clin Invest* 110:448–453 (1987).

Sawada, et al.: Available removal systems—state of the art, in Nydegger UE(ed), Therapeutic Hemapheresis in the 1990, New York, Karger: 51–113 (1990).

Schurig, R, et al.: Hemodynamic studies in long-term peritoneal dialysis patients. *Artific Organs* 3:215–218 (1979).

Stephen, R L, et al.: Recirculating peritoneal dialysis with subcutaneous catheter. *Trans Am Soc Artif Intern Organs* 22:575–585 (1976).

Tsilibary, F C, et al.: Absorption from the peritoneal cavity: SEM study of the mesothelium covering the peritoneal surface of the muscular portion of the diaphragm. *Am J Anat* 2:127–133 (1977).

Tsilibary, F C, et al.: Absorption from the peritoneal cavity: SEM study of mesothelium covering the peritoneal surface of the muscular portion of the diaphragm. .*Am J Anat* 180:195 (1987).

Twardowski, Z J: *Transport Kinetics. Peritoneal Dialysis*, 133–151, Kluwer Academic Publishers (1989).

Urbaniak S J, et al.: Theraputic apheresis. *British Med J* 300:662–665 (1990).

Verger, C, et al.: Acute changes in peritoneal morphology and transport properties with infectious peritonitis and mechanical injury. *Kid Int* 23:823 (1983).

Verger, C, et al.: *Peritoneal ultrastructure.* In: KD Nolph(ed) Peritoneal Dialysis, Martinus Nijhoff, Boston: 93–113 (1985).

Wayland, H: Transmural and interstitial molecular transport. Proc Int'l CAPD Symp. Paris, 1979. *Excerpta Medica:*18–27 (1980).

Wayland, H: Action of Histamine on the microvasculature. Proc 1st CAPD Int Symp. *Excerpta Medica, Amsterdam:*18–27 (1980).

Zelman, A, et al.: Augmentation of peritoneal dialysis efficiency with programmed hyper/hypoosmotic dialysates. *ASAIO Trans* 23:203–209 (1977).

Zong-da M, et al.: A serological study of hepatitis C infection in plasmapheresis donors. *Chinese Medical J* 104:494–497 (1991).

Changes may be made in the construction, operation and arrangement of the various parts, elements, steps and procedures described herein without departing from the concept and scope of the invention as defined in the following claims.

What is claimed is:

1. A method for removing plasma components from a patient, the method comprising serial instilling and draining of a first physiologic solution with added vasodilator drug, in the patient's peritoneal cavity followed by serial instilling and draining of a second physiologic solution with added vasoconstrictor drug in the patient's peritoneal cavity.

2. The method of claim 1 wherein instilling and draining of the first physiologic solution occur simultaneously, instilling occurring through a first peritoneal catheter and draining occurring through a second peritoneal catheter, said first and second catheters being implanted in the patient's peritoneal cavity.

3. The method of claim 1 wherein instilling and draining of the second physiologic solution occur simultaneously, instilling occurring through a first peritoneal catheter and draining occurring through a second peritoneal catheter, said first and second catheters being implanted in the patient's peritoneal cavity.

4. A method of removing plasma components from a patient's circulating blood using first and second physiologic solutions, the method comprising the steps:

instilling a first physiologic solution with added vasodilator drug into a patient's peritoneal cavity, said vasodilator drug being in an amount effective to increase passage of plasma components into the solution;

allowing the first solution to remain in the peritoneal cavity for a first dwell time sufficient to remove plasma components from the patient's circulating blood;

draining the first solution from the peritoneal cavity;

instilling a second physiologic solution with added vasoconstrictor drug into the patient's peritoneal cavity, said vasoconstrictor drug being in an amount effective to prevent material reduction in rate of removal of plasma components from the patient's circulating blood;

allowing the second solution to remain in the peritoneal cavity for a second dwell time sufficient to effect removal of plasma components from the patient's circulating blood; and draining the second solution from the peritoneal cavity.

5. The method of claim 1 or 4 wherein the first physiologic solution with added vasodilator drug is employed for serial instilling and draining until an effective amount of plasma components is no longer removed during draining, after which the second physiologic solution with added vasoconstrictor drug is employed for serial instilling and draining until local peritoneal compensation effects induced by the first physiologic solution are effectively reduced, after which the first physiologic solution is employed again et seq.

6. The method of claim 1 or 4 wherein instilling and draining of the first physiologic solution is alternated with instilling and draining of the second physiologic solution.

7. The method of claim 1 or 4 wherein the first physiologic solution comprises plasma proteins.

8. The method of claim 1 or 4 wherein the second physiologic solution comprises plasma proteins.

9. The method of claim 1 or 4 wherein the first physiologic solution is hypertonic and the second physiologic solution is hypotonic.

10. The method of claim 1 or 4 wherein tonicity of the first and second physiologic solutions is hypotonic if the patient is hypovolemic prior to instilling of the solution; and hypertonic if the patient is hypervolemic prior to instilling of the solution.

11. The method of claim 1 or 4 wherein plasma expander is administered intravenously.

12. The method of claim 11 wherein plasma expander is administered while the patient is asleep.

13. The method of claim 1 or 4 wherein instilling and draining of the first physiologic solution is followed by instilling and draining of a third physiologic solution containing no added vasodilator or vasoconstrictor, followed by instilling and draining of the second physiologic solution.

14. The method of claim 13 wherein the third physiologic solution is hypotonic.

15. The method of claim 13 wherein the third physiologic solution is hypertonic.

16. The method of claim 13 wherein the third physiologic solution comprises plasma expander.

17. The method of claim 13 wherein tonicity of the third physiologic solution is
hypotonic if the patient is hypovolemic prior to instilling of the solution; and
hypertonic if the patient is hypervolemic prior to instilling of the solution.

18. The method of claim 13 wherein the third physiologic solution is employed for serial instilling and draining until an effective amount of plasma components is no longer removed during draining.

19. The method of claim 1 or 4 further comprising administering an anticoagulant to the patient in an amount and for a time effective to prevent clogging of a peritoneal dialysis catheter or of peritoneal membrane pores.

20. The method of claim 19 wherein the anticoagulant is administered intravenously by bolus.

21. The method of claim 19 wherein the anticoagulant is administered subcutaneously.

22. The method of claim 19 wherein the anticoagulant is heparin.

23. The method of claim 19 wherein the anticoagulant is administered orally.

24. The method of claim 1 or 4 wherein the plasma components comprise plasma proteins.

25. The method of claim 1 or 4 wherein the vasoconstrictor drug is norepinephrine.

26. The method of claim 1 or 4 wherein the vasodilator drug is dipyridamole.

27. The method of claim 1 or 4 wherein the vasodilator drug is sodium nitroprusside.

28. The method of claim 1 or 4 wherein the vasodilator drug is histamine phosphate.

29. The method of claim 1 or 4 wherein the vasodilator drug is dibenzyline.

30. The method of claim 1 or 4 further comprising the step of intermittently administering an anticoagulant intravenously.

31. The method of claim 1 or 4 further comprising the step of adding an anticoagulant drug to the physiologic solution for infusion into the peritoneal cavity.

32. The method of claims 1 or 4 wherein proteins are selectively removed from the drained solution, after which the drained solution is reused.

33. The method of claim 1 or 4 wherein proteins are selectively removed from the peritoneal cavity by adding absorbent to the first and second solutions.

34. The method of claim 1 or 4 wherein plasma proteins removed from the peritoneal cavity are concentrated, separated and selectively readministered to the patient.

35. The method of claim 4 wherein all of the steps are repeated.

36. The method of claim 4 further comprising the step of intermittently adding effective amounts of vasodilator drug at intervals during the first dwell time.

37. The method of claim 4 further comprising the step of intermittently adding effective amounts of vasoconstrictor drug at intervals during the second dwell time.

38. The method of claim 4 further comprising the step of continuously adding effective amounts of vasodilator drug at intervals during the first dwell time.

39. The method of claim 4 further comprising the step of continuously adding effective amounts of vasoconstrictor drug at intervals during the second dwell time.

40. The method of claim 4 wherein the first and second dwell times are about 30 minutes.

41. The method of claim 4 wherein the first and second dwell times are about 1.5 hours.

42. The method of claim 4 wherein the first and second dwell times are about 4 hours.

43. The method of claim 4 wherein the first and second dwell times are about 8 hours.

* * * * *